US011517790B2

(12) United States Patent
Carpenter et al.

(10) Patent No.: US 11,517,790 B2
(45) Date of Patent: Dec. 6, 2022

(54) METHODS AND APPARATUS FOR TRAINING PLAN DELIVERY AND LOGGING

(71) Applicant: MYFITNESSPAL, INC., San Francisco, CA (US)

(72) Inventors: Kaitlyn Carpenter, Austin, TX (US);
Bradford J. Fults, Austin, TX (US);
Jeff Knight, Austin, TX (US)

(73) Assignee: MyFitnessPal, Inc., San Francisco, CA (US)

( * ) Notice: Subject to any disclaimer, the term of this patent is extended or adjusted under 35 U.S.C. 154(b) by 363 days.

(21) Appl. No.: 16/696,232

(22) Filed: Nov. 26, 2019

(65) Prior Publication Data
US 2021/0154530 A1 May 27, 2021

(51) Int. Cl.
*G16H 20/30* (2018.01)
*A63B 24/00* (2006.01)

(52) U.S. Cl.
CPC ...... *A63B 24/0062* (2013.01); *A63B 24/0075* (2013.01); *G16H 20/30* (2018.01); *A63B 2225/50* (2013.01); *A63B 2230/06* (2013.01)

(58) Field of Classification Search
CPC combination set(s) only.
See application file for complete search history.

(56) References Cited
U.S. PATENT DOCUMENTS 10,258,288 B2 * 4/2019 Penders ............... A61B 5/7221
10,300,334 B1   5/2019 Chuang
10,878,952 B1 * 12/2020 Patel .................. G06K 7/10297
11,056,238 B1 *  7/2021 Nakajima .............. G16H 40/67
11,062,591 B1 *  7/2021 Cascioli .............. G08B 29/188
11,151,888 B1 * 10/2021 Fillinger .............. G06Q 20/308
11,217,341 B2 *  1/2022 Hope ................... G16H 20/30
11,217,343 B2 *  1/2022 Lee ...................... G16H 20/30
2007/0011919 A1   1/2007 Case
(Continued)

OTHER PUBLICATIONS

U.S. Appl. No. 16/691,849 to Carpenter et al., filed Nov. 22, 2019.
(Continued)

*Primary Examiner* — Sundhara M Ganesan
(74) *Attorney, Agent, or Firm* — Maginot, Moore & Beck, LLP

(57) ABSTRACT

Systems, apparatus, and methods for training plan delivery and workout logging. In one embodiment of the present disclosure, a fitness tracking system and/or community of personal devices: (i) generates a training plan, (ii) schedules and coordinates delivery of workouts based on the training plan, and (iii) notifies the user of workouts via one or more wearables. In one exemplary embodiment, a fitness tracking system generates a training plan based on user workout history and/or user input. Thereafter, suggested workouts can be pushed to the user's community of personal devices, via a coordinating device (e.g., a smart phone). The coordinating device manages and controls workout notifications for any available coordinated devices (e.g., smart watches, smart shoes, etc.) Unlike previous systems, the disclosed embodiments of the present disclosure integrate a community of different personal devices together so as to capture activity tracking data regardless of what a user is wearing.

20 Claims, 8 Drawing Sheets

(56) References Cited

U.S. PATENT DOCUMENTS

| | | | |
|---|---|---|---|
| 2009/0047645 A1 | 2/2009 | Dibenedetto et al. | |
| 2011/0214030 A1* | 9/2011 | Greenberg | A61B 5/7257 714/748 |
| 2012/0274508 A1 | 11/2012 | Brown et al. | |
| 2014/0107932 A1* | 4/2014 | Luna | G16H 50/20 702/19 |
| 2014/0200691 A1 | 7/2014 | Lee et al. | |
| 2014/0343380 A1* | 11/2014 | Carter | A61B 5/4806 600/595 |
| 2014/0350883 A1* | 11/2014 | Carter | A61B 5/02438 702/141 |
| 2015/0281364 A1* | 10/2015 | Connolly | G06Q 10/06 709/217 |
| 2015/0358767 A1* | 12/2015 | Luna | G01S 5/0263 455/456.1 |
| 2017/0020444 A1* | 1/2017 | Lurie | A61B 5/74 |
| 2018/0042542 A1* | 2/2018 | Cronin | A61B 5/4803 |
| 2018/0114124 A1* | 4/2018 | Cronn | G04G 21/00 |
| 2018/0336530 A1 | 11/2018 | Johnson et al. | |
| 2019/0105535 A1 | 4/2019 | Kovach et al. | |
| 2019/0254522 A1* | 8/2019 | Brancaccio | G06F 9/453 |
| 2020/0005928 A1* | 1/2020 | Daniel | G16H 15/00 |
| 2020/0016457 A1* | 1/2020 | Ben-Chanoch | A63B 24/0006 |
| 2020/0075152 A1* | 3/2020 | Radovcic | G16H 20/60 |
| 2020/0075167 A1* | 3/2020 | Srivastava | G16H 20/30 |
| 2020/0105404 A1* | 4/2020 | Major | G16H 20/30 |
| 2020/0113518 A1* | 4/2020 | Mollohan | A63B 22/025 |
| 2020/0160961 A1* | 5/2020 | Wadhawan | A63B 24/0059 |
| 2020/0167815 A1* | 5/2020 | Naik | A61B 5/1118 |
| 2020/0211410 A1* | 7/2020 | Kang | G06Q 30/02 |
| 2020/0250508 A1* | 8/2020 | De Magalhaes | G16H 50/30 |
| 2020/0275394 A1* | 8/2020 | Lam | H04W 76/40 |
| 2020/0297269 A1* | 9/2020 | Vieri | G16H 40/67 |
| 2020/0405158 A1* | 12/2020 | Jeong | G16H 50/30 |
| 2020/0411159 A1* | 12/2020 | Chien | G06F 3/011 |
| 2021/0026440 A1* | 1/2021 | Poupyrev | G06F 3/011 |
| 2021/0043301 A1* | 2/2021 | Goel | G16H 40/63 |
| 2021/0093919 A1* | 4/2021 | Lyke | G16H 50/20 |
| 2021/0125728 A1* | 4/2021 | Dessaud | A61B 5/024 |
| 2021/0146195 A1* | 5/2021 | Szpiczynski | G16H 40/63 |
| 2021/0153805 A1 | 5/2021 | Carpenter et al. | |
| 2021/0174971 A1* | 6/2021 | Jain | G16H 20/10 |
| 2021/0236025 A1* | 8/2021 | Comtois | A61B 5/6812 |
| 2021/0241649 A1* | 8/2021 | Kinnunen | G16H 20/30 |
| 2021/0330211 A1* | 10/2021 | Han | A63B 24/0062 |
| 2022/0022778 A1* | 1/2022 | Gauthier | A61B 5/1118 |

OTHER PUBLICATIONS

Garmin, Image of three watches with graphical user interface, available on or before Jul. 31, 2019, npl_ref1_Garmin_1).
Garmin, Image of watch with graphical user interface, available on or before Jul. 31, 2019, (npl_ref2_Garmin_2).
Polar, Image of watch with graphical user interface, available on or before Jul. 31, 2019, (npl_ref3_Polar).
Suunto, Image of watch with graphical user interface, available on or before Jul. 31, 2019, (npl_ref4_Suunto_1).
Suunto, Image of two watches with graphical user interface, available on or before Jul. 31, 2019, npl_ref5_Suunto_2).
Suunto, Image of watch with graphical user interface, available on or before Jul. 31, 2019, (npl_ref6_Suunto_3).
Suunto, Image of watch with graphical user interface, available on or before Jul. 31, 2019, (npl_re17_Suunto_4).

* cited by examiner

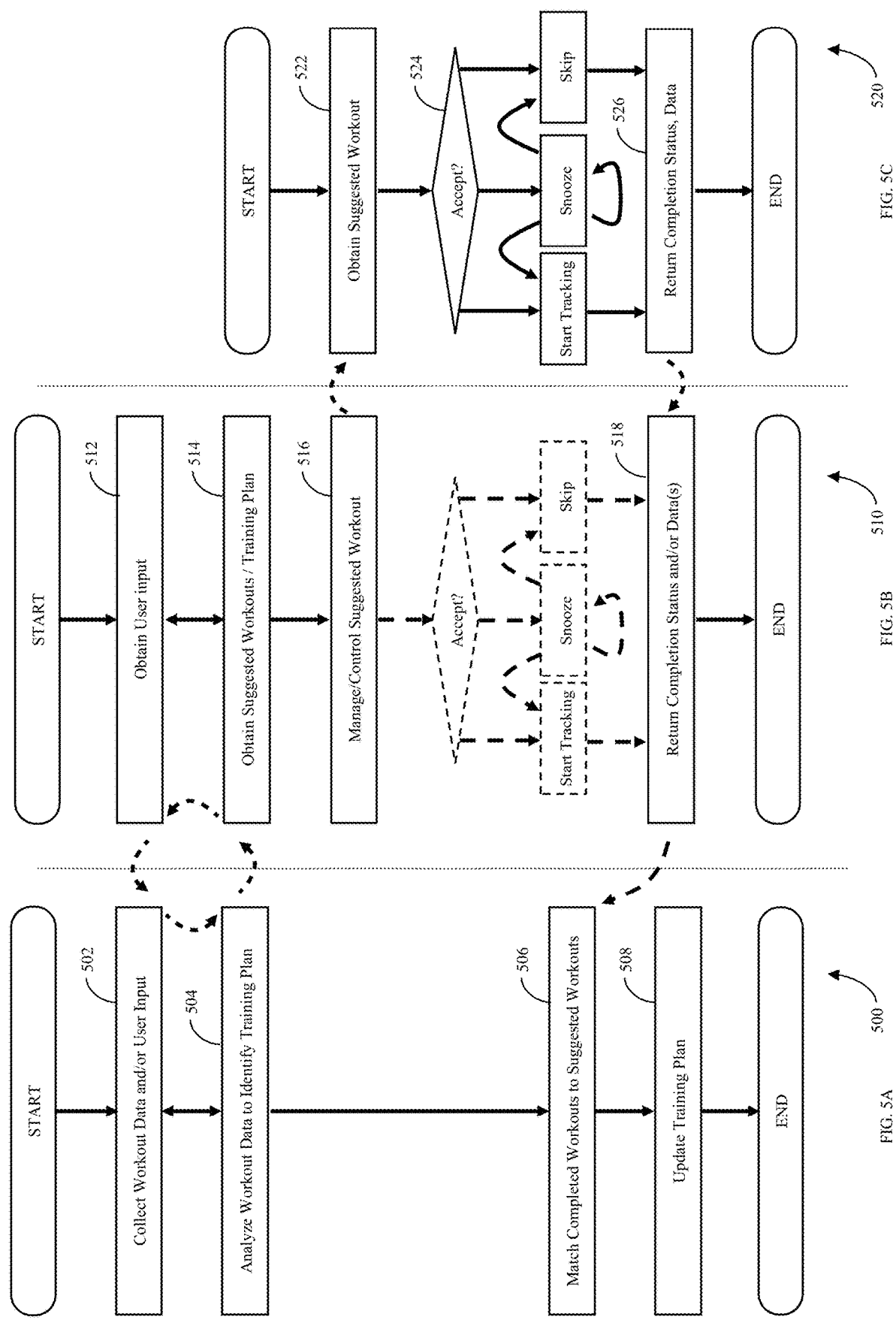

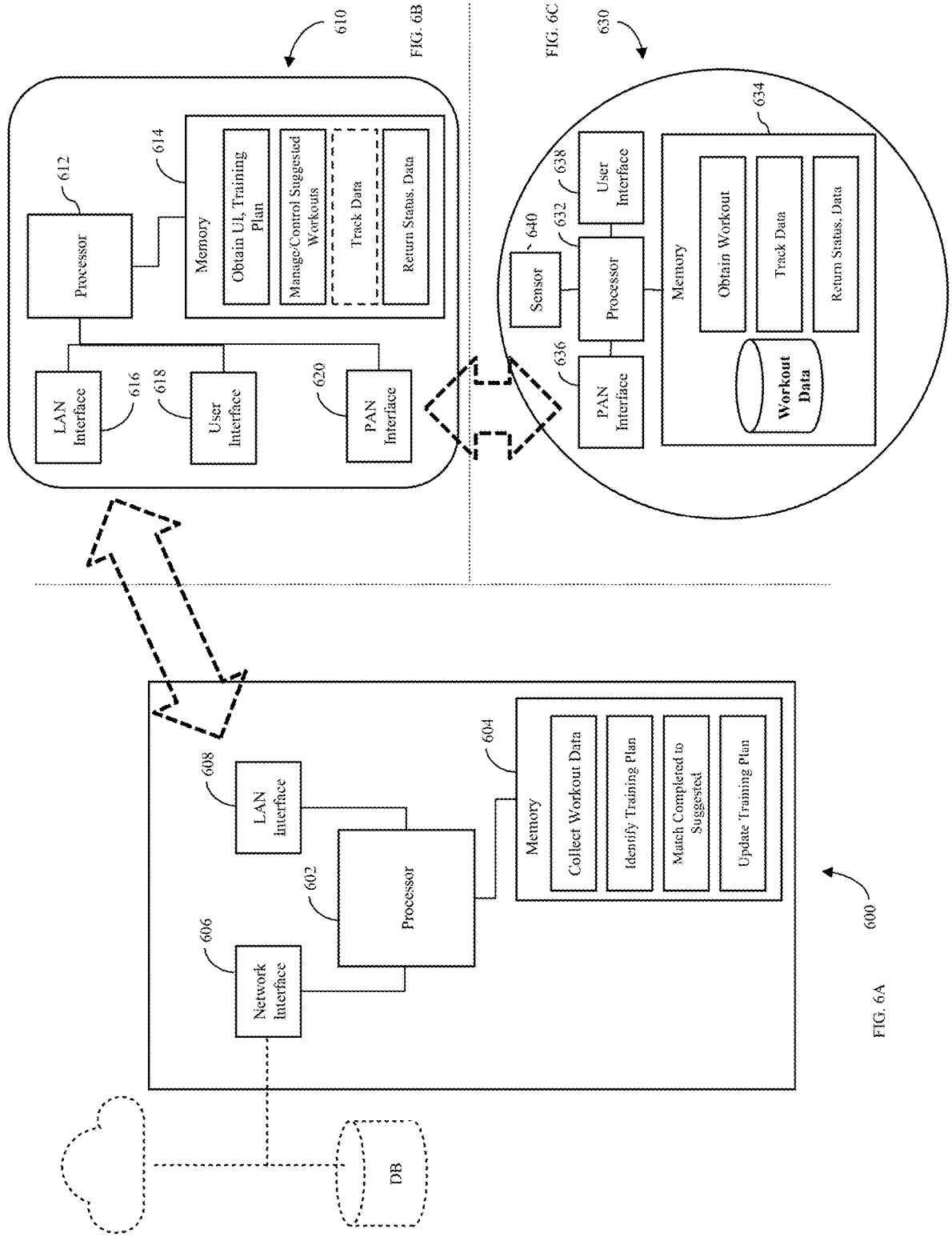

METHODS AND APPARATUS FOR TRAINING PLAN DELIVERY AND LOGGING

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

TECHNICAL FIELD

This disclosure relates generally to the field of personal fitness. More particularly, the present disclosure relates to systems, computer programs, devices, and methods for delivering suggested workouts to a user.

DESCRIPTION OF RELATED TECHNOLOGY

In recent years, health and fitness tracking applications that track user workouts and activities have become very popular. Routine physical activity is important to a healthy lifestyle and is known to prevent and/or ameliorate various health conditions, such as diabetes and obesity. Health and fitness tracking applications allow users to set and achieve personalized health goals by tracking the amount of physical activity, regularity of physical activity, and/or intensity of physical activity. These applications enable users to gain insights regarding their workout regimen efficacy.

Existing wearable devices have broad differences in form and function. Coordinating activity tracking across different wearable devices is problematic.

SUMMARY

The present disclosure addresses the foregoing needs by disclosing, inter alia, methods, devices, systems, and computer programs for delivering suggested workouts in accordance with a training plan to a community of personal devices, thereby enabling users to set and achieve personalized health goals regardless of what they are wearing.

In one aspect, a method for coordinating delivery of suggested workouts to a user is disclosed. In one embodiment, the method includes: obtaining a plurality of training plans from a fitness tracking system; obtaining user input identifying a selected training plan from the plurality of training plans; obtaining one or more suggested workouts corresponding to the selected training plan; providing the one or more suggested workouts to a first coordinated personal device of a community of coordinated personal devices; obtaining a first workout data record indicating a completion status of a first suggested workout of the one or more suggested workouts; and providing the first workout data record to the fitness tracking system.

In one variant, the method further includes providing a second suggested workout to a second coordinated device of the community of personal devices; and receiving a second workout data record.

In one variant, the method further includes modifying at least one suggested workout associated with the selected training plan. In one such variant, modifying the at least one suggested workout includes modifying a goal, a date, or a performance metric.

In one variant, the method further includes matching the first workout data record to the first suggested workout based on a unique workout identifier or a data content.

In one variant, providing the one or more suggested workouts to the first coordinated personal device includes: checking an availability of the first coordinated personal device; and sending the one or more suggested workouts to the first coordinated personal device when available.

In one aspect, a method for suggesting workouts to a user is disclosed. In one embodiment, the method includes: providing a plurality of training plans to a coordinating device; obtaining a user selected training plan; providing a plurality of suggested workouts to the coordinating device based on the user selected training plan; obtaining a plurality of workout data records from the coordinating device; each of the plurality of workout data records corresponding to a respective one of the plurality of suggested workouts; matching the plurality of workout data records to their corresponding respective one of the plurality of suggested workouts based on an identified similarity; and re-assessing the user selected training plan based on the plurality of workout data records.

In one variant, the user selected training plan is based on a user workout history.

In one variant, the identified similarity includes: a unique workout identifier, goal, or performance metrics.

In one variant, the plurality of workout data records are generated by a community of personal devices in communication with the coordinating device; and the method further includes reconciling data records generated by different devices in the community of personal devices from the plurality of workout data records. In one such variant, reconciling the data records is based on a hierarchical priority of the community of personal devices.

In one variant, the identified similarity is based on multivariate matching logic.

In one variant, the plurality of workout data records includes completion statuses; and re-assessing the user selected training plan is based on at least one completion status.

In one variant, the plurality of workout data records includes captured workout metrics; and re-assessing the user selected training plan is based on at least one captured workout metric compared to an expected physiological progress.

In one aspect, a non-transitory computer-readable medium is disclosed. In one embodiment, the non-transitory computer-readable medium includes one or more instructions, that when executed by a processor, causes a user apparatus to: obtain one or more suggested workouts corresponding to a selected training plan; provide the one or more suggested workouts to a first coordinated device of a community of coordinated personal devices; receive a first workout data record indicating an intended completion status of a first suggested workout of the one or more suggested workouts; and provide the intended completion status to a fitness tracking system.

In one variant, the non-transitory computer-readable medium, further includes one or more instructions, that when executed by the processor, causes the user apparatus to send a notification to a user of the one or more suggested workouts via a user interface. In one such variant, the one or more instructions, when executed by the processor, causes the user apparatus to return a completed workout data record that augments the intended completion status when the first suggested workout was performed differently than suggested. In one specific implementation, the one or more instructions, when executed by the processor, causes the user apparatus to responsive to the user accepting the first suggested workout, capture one or more workout metrics via a sensor.

In one variant, the non-transitory computer-readable medium, further includes one or more instructions, that when executed by the processor, causes the user apparatus to determine an availability of the first coordinated device of the community of personal devices; and push the first suggested workout to the first coordinated device when available.

In one variant, the non-transitory computer-readable medium, further includes one or more instructions, that when executed by the processor, causes the user apparatus to responsive to matching the first workout data record from the first coordinated device with the first suggested workout, return the first workout data record and an identification of a match.

More generally, various aspects of the present disclosure are directed to systems, apparatus, methods and storage media which suggest (notify), coordinate, and/or track workouts in accordance with a training plan within a community of personal devices.

Other features and advantages of the present disclosure will immediately be recognized by persons of ordinary skill in the art with reference to the attached drawings and detailed description of exemplary embodiments as given below.

BRIEF DESCRIPTION OF THE DRAWINGS

FIGS. 2A-2C are exemplary graphical representations of a wearable user interface, consistent with the various principles described herein.

FIGS. 5A-5C are logical flow diagrams of exemplary methods for suggesting workouts to a user, coordinating delivery of suggested workouts to a user, and tracking workouts via a personal device, in accordance with the various principles described herein.

FIGS. 6A-6C are logical block diagrams of exemplary server apparatus, coordinator device, and personal device, in accordance with the various principles described herein.

Figure 1:
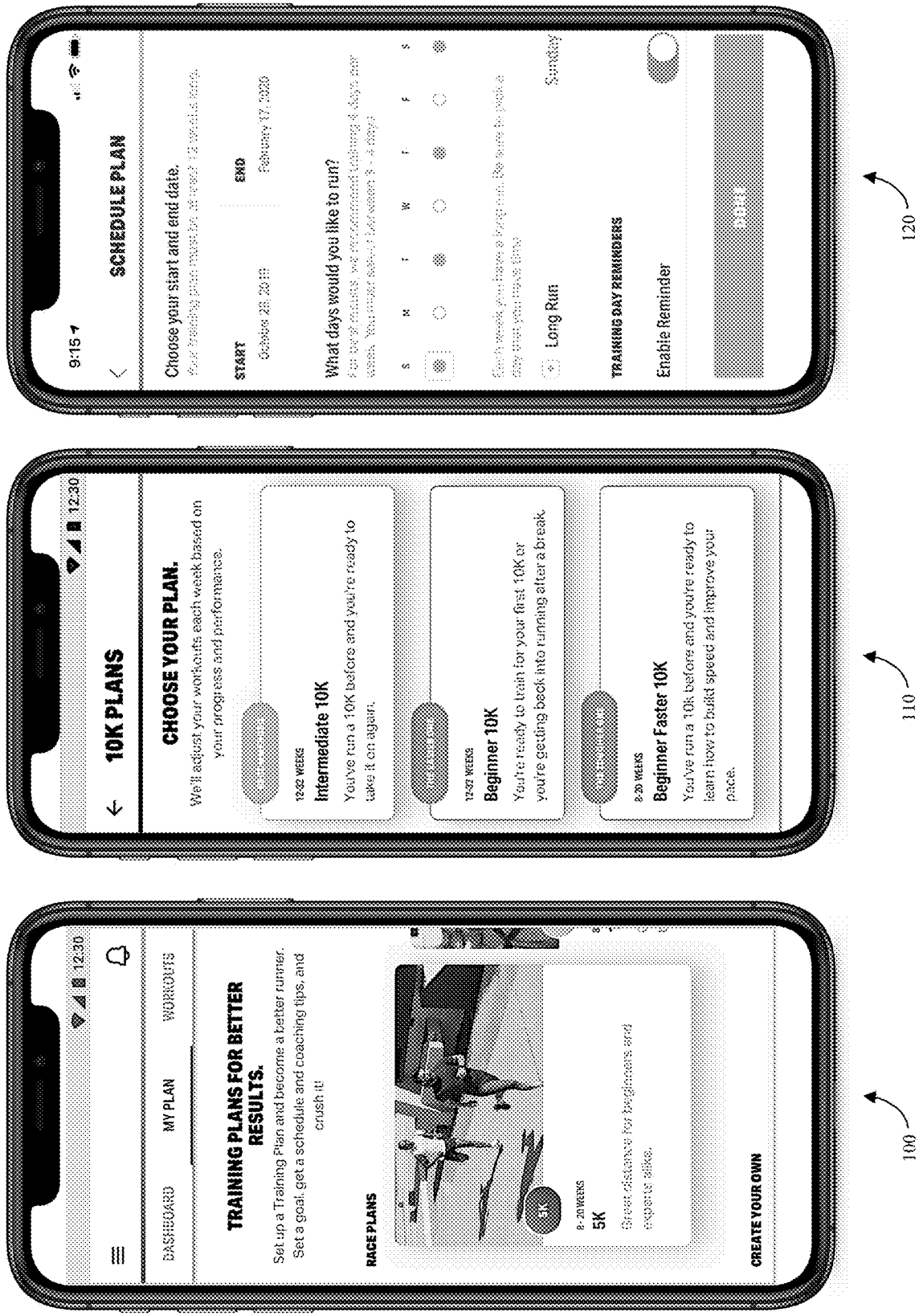
FIG. 1 is a graphical representation of a user interface useful for identifying personal fitness goals and setting a training plan, consistent with the various principles described herein.

All Figures© Under Armour, Inc. 2019. All rights reserved.

DETAILED DESCRIPTION

Disclosed embodiments include systems, apparatus, methods and storage media which coordinate suggested workout delivery based on a training plan, and log workouts within a community of personal devices.

In the following detailed description, reference is made to the accompanying drawings which form a part hereof wherein like numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without departing from the spirit or scope of the present disclosure. It should be noted that any discussion herein regarding "one embodiment", "an embodiment", "an exemplary embodiment", and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C). Similar logic applies to the use of the term "or" herein; i.e., "A or B" means (A), (B), or (A and B).

The terms "comprising," "including," "having," and the like, as used with respect to embodiments of the present disclosure, are synonymous.

Wearables, Fitness Tracking Devices, and Consumer Electronics

Regular workouts and accurate fitness tracking are important to measure progress towards a user's individual fitness goals. People have historically tracked workouts and fitness regimens on physical media (paper, chalkboard, whiteboard, etc.); more recently, however, the ubiquity of consumer electronics has enabled users to track progress electronically. Modern fitness tracking applications greatly improve progress and workout retention by offering convenient features such as e.g., tracking workouts, workout recommendations, and/or workout scheduling.

One burgeoning field in consumer electronics is the so-called "wearables" market. Wearable devices are intended to be worn during everyday activity; usually, wearable devices trade-off functionality, user accessibility, and/or processing power for other considerations e.g., style, aggressive form factors, reduced power consumption, and durability (weather resistance, etc.) For example, a smart watch or smart shoes may focus on style and fit rather than e.g., a large screen or high-performance processing.

Advantageously, the ruggedization of wearable devices makes them uniquely suited for fitness tracking applications in a way that other consumer electronics are not. For example, modern smart phones are not designed to be struck, dropped, or subjected to the harsh elements (rain, water, etc.) Moreover, wearable form factors minimally interfere with movement and/or mobility e.g., wearables are not "held" with hands nor do they distract from the user's attention. In particular, most wearables are designed to unobtrusively use e.g., tactile, haptic, auditory, and/or time-insensitive visual interfaces.

Unfortunately, the wearables market is a recent phenomenon and has not yet achieved market maturity. As a practical matter, fast changing market pressures and competition continually force wearable manufacturers to diversify and specialize in emerging market niches. Additionally, the lack of well understood usage means that many wearables utilize immature and/or proprietary protocols for communication. For example, a smart watch and a smart shoe may both be able to track steps, but the shoe's data may be more accurate than the smart watch (the shoe senses footsteps, the watch infers steps from arm movement) or vice versa. Similarly, different wearables may provide related data on a similar activity e.g., a smart shoe may count steps, whereas a smart phone may track GPS location (e.g., distance run). Combining and/or reconciling disparities in measured data may greatly complicate data analytics and/or cause user confusion.

Furthermore, variability in personal taste, device capability, and/or the realities of everyday wear also present unique new problems for wearable devices. People don't wear the same outfits every day, and by extension, may not wear the same wearable every day. As a related issue, human users have wide ranging habits and behaviors. For instance, a user may alternate usage between wearables having similar functionality; e.g., a user may occasionally use a smart watch to count steps and use a smart shoe to count steps at other times.

More directly, while wearables (in aggregate) have the potential to capture a much larger and/or more precise body of activity tracking data, each wearable (when individually considered) may wildly fluctuate in usage and/or accuracy. In view of the limitations of the existing activity tracking device ecosystem, there exists a persistent need to enable activity tracking regardless of what a user is wearing.

Example Operation

Various embodiments of the present disclosure utilize the available devices of the user's community of personal devices to suggest (notify), coordinate, and/or track workouts in accordance with a training plan. In one embodiment of the present disclosure, a fitness tracking system and/or community of personal devices: (i) enable a user to select a training plan, (ii) schedules and coordinates delivery of workouts based on the training plan, and (iii) notifies the user of workouts via one or more wearables. In one exemplary embodiment, a fitness tracking server analyzes the user's historic workout data and/or personal fitness goals to recommend a training plan to a user. The user can accept, create, reject, select, and/or modify preferences for the recommended training plan. Subsequently thereafter, suggested workouts are pushed to one or more of the user's wearable devices, based on the training plan. Actual workout data is tracked by the wearable and recorded in workout data records; the workout data records can be "matched" against the suggested workout. User progress is updated at the coordinating device and/or fitness tracking server, and subsequent re-assessments and updates to the user's suggested workouts can be recommended based on actual tracked progress in the training plan across the community of personal devices.

FIG. 1 shows exemplary graphical representations of a user interface useful for identifying personal fitness goals and setting a training plan, consistent with the various principles described herein. As depicted in screenshot 100, a user can select a desired outcome (e.g., to become a better runner). The user may be presented with a few measurable goals of increasing specificity and/or customization options (e.g., "5 K", "10 K", "create your own", etc.) In some cases, the measurable goals may provide the user with some motivational text and/or useful information (e.g., "5 K: Great distance for beginners and experts alike").

Once a measurable goal is selected, the user can identify a specific training plan to achieve the measurable goal. In one exemplary implementation, the user may be recommended a training plan based on the user's previous workout history and/or other personal fitness data; for instance, a user that has successfully run a 5 K may be recommended an "Intermediate 10 K" plan. In some cases, the user may be offered a few similar training plans (e.g., in the illustrated screenshot 110: "Beginner 10 K", "Beginner Faster 10 K"). A variety of schemes may be used to recommend training plans; for example, recommendations may be based on e.g., an initial calibration workout, default parameters, user history, training plans popular with the peers, etc.

After the user has selected a training plan, the user may further customize workout suggestion associated with the training plan for their practical considerations (e.g., schedule availability and/or other constraints). In the exemplary screenshot 120, the user may select a start and/or end date, weekly schedule, and/or other preferences (e.g., Sundays may be reserved for long runs, etc.) In some cases, the user may additionally tailor other user experience (UX) parameters such as: notification time, notification type (haptic, audible, visual, etc.), workout "snoozing" (postpone for a wait time, postpone to a set time), etc. In the illustrated example, the fitness tracking server and/or coordinating device of FIG. 1 generate suggested workouts based on the training plan, starting Oct. 28, 2019-Feb. 17, 2020, for every Sunday, Tuesday, Thursday, and Saturday in accordance with the training plan. In one exemplary embodiment, the training plan may additionally include periodic re-assessments discussed in greater detail hereinafter.

Once selected, the user's preferences and associated training plan are stored at the fitness tracking system for delivery via the user's coordinating device (e.g., a smart phone). The coordinating device serves as a centralized point of contact for the user's community of personal devices. Suggested workouts can be pushed and/or workout data records can be pulled via the coordinating personal device; the coordinating device dynamically manages delivery based on personal device availability.

In one exemplary embodiment, the coordinating device may have multiple ways to notify a user of a suggested workout. In a first mode, the coordinating device can push a suggested workout to an available wearable device (e.g., a smart phone to a paired smart watch). In a second mode, the coordinating device can use an in-application notification (e.g., the smart phone's native "in-app" notification system).

In one exemplary embodiment, once the user accepts the suggested workout notification (in either the wearable notification or the in-app notification), then the coordinating device pre-loads a target goal to the wearable device. The wearable device tracks the user's progress during the workout and generates a workout data record thereafter.

Notably, not all wearables may capture workout data, and in some cases matching suggested workouts with captured metrics from legacy wearables may be complex, error prone, and/or unnecessary. Thus, in one exemplary embodiment, a suggested workout that is "accepted" automatically generates an intended completion data record. In such cases, the intended completion data record may include null data records and/or use default workout metrics (e.g., an untracked "8 km run" may be logged with the default distance of 8 km, etc.) Intended completion data records may be later augmented with captured data, user provided data, etc.

Various embodiments of the present disclosure may additionally monitor completion status (not just captured metrics). As but one example, a user that misses a string of workouts may be prompted to explain why the suggested workouts were missed, such that useful corrections can be made. Different user feedback may result in different corrections; e.g., a user that reports injury may be managed differently than a user that feels like they have "plateaued." In some variants, continued deviations from the training plan may trigger "coachable moment" type question-response exercises (where a user is invited to re-evaluate their fitness goals and motivations). In other variants, corrective action may ask the user to re-select a different training plan so as to re-align actual performance with expected performance.

Figure 2A:
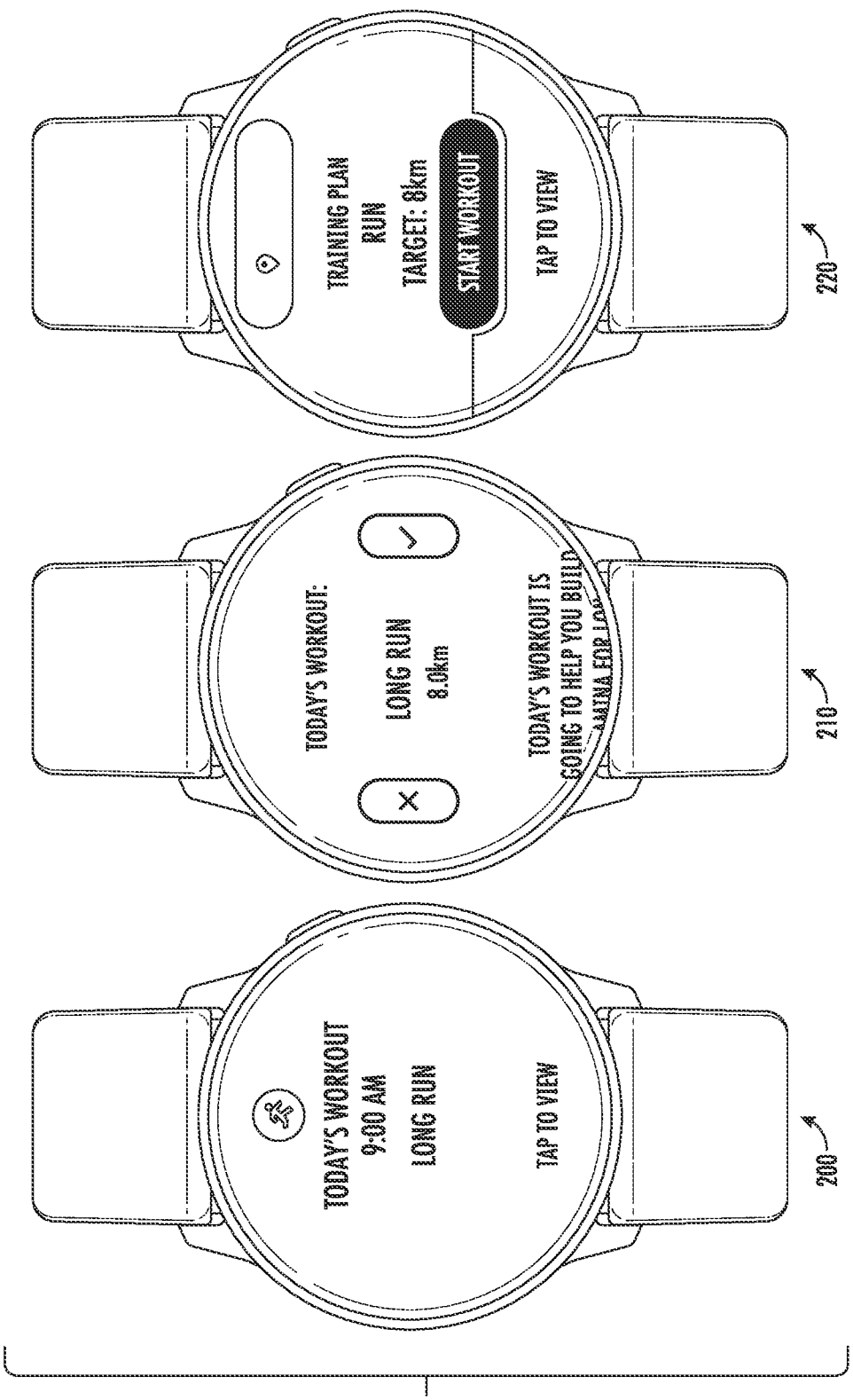

Referring now to FIG. 2A, exemplary graphical representations of a wearable user interface useful for notifying a user of a workout is shown consistent with the various principles described herein. As depicted in screenshot 200, the smart watch receives a notification of a workout. The notification may include a brief description (e.g., "Long Run", etc.) as well as scheduling information. The wearable's unobtrusive notification does not require immediate attention (e.g., the user can tap to view the workout at their convenience). When ready, the user may view the workout notification in more detail (screen shot 210). In the illustrated embodiment, the workout notification includes text to motivate the user (e.g., "Long Run 8.0 km"). The user can be prompted to accept, decline, or "snooze" (postpone the workout to a later time, etc.) If the user accepts the workout, then the user can start tracking their workout (screen shot 220).

FIG. 2B illustrates various screen shots that may be provided to the user during the workout. For example, in the illustrated "Long Run" example, the user may be able to view distance, pace (peak and average), duration, cadence (peak and average), heart rate (peak and average), location, and/or progression. Artisans of ordinary skill in the related arts will readily appreciate that the foregoing information is specific to running workouts, and that other types of user interface information would be relevant for other workout types. For example, a weightlifting workout may identify e.g., repetitions, sets, etc. Similarly, in multi-staged workouts (e.g., a "triathlon" type workout with a run stage, a bike stage, a swim stage, etc.) each stage of the workout can be separately completed with different captured metrics.

Figure 2C:
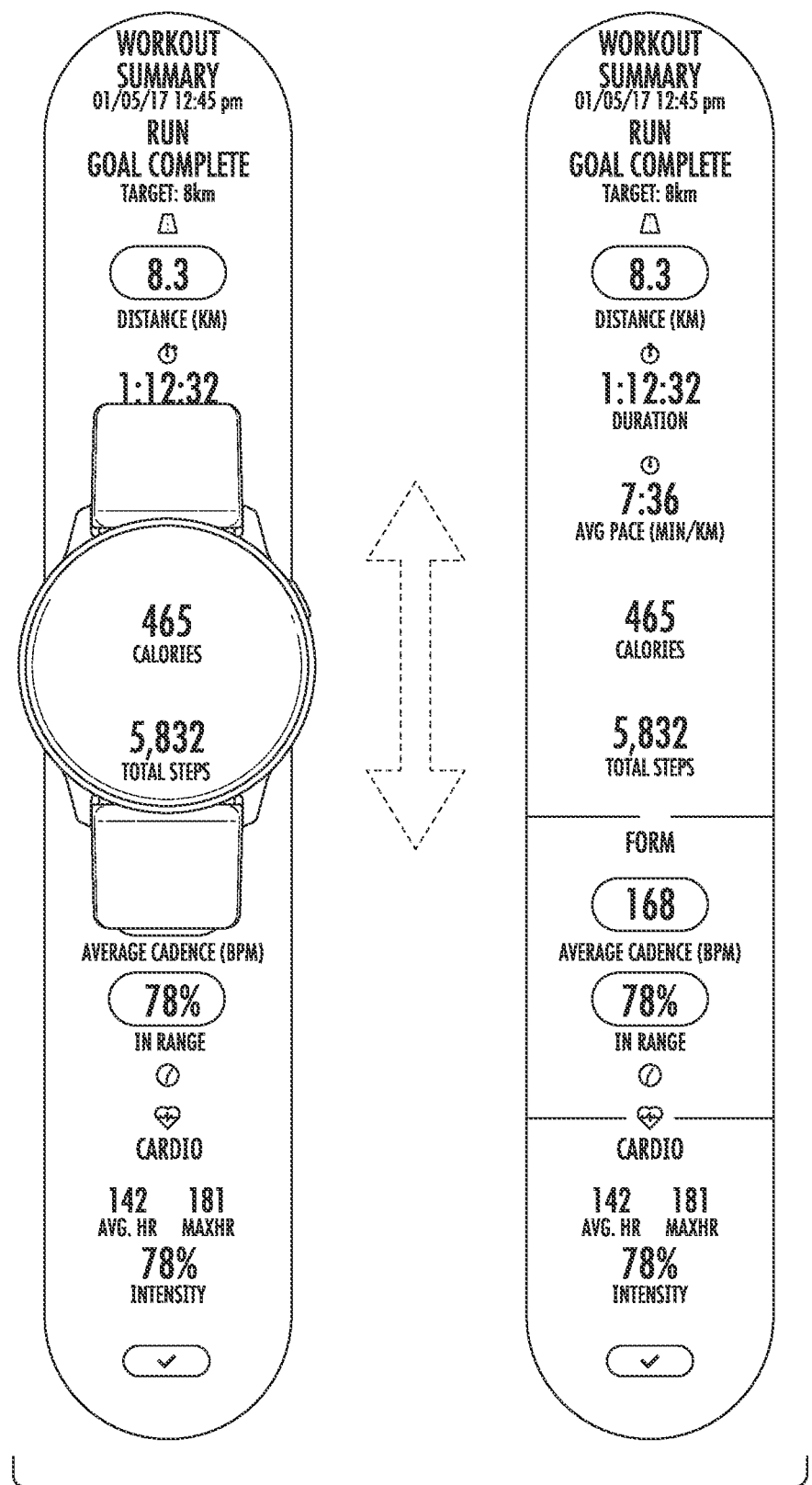

After the workout, the captured metrics of the workout data record may be displayed via a workout summary. For example, as shown in the user interface of FIG. 2C, the wearable may summarize actual distance run, actual duration, average (and/or peak) pace, average (and/or peak) cadence, estimated calories, steps counted, average (and/or peak) heart rate, range (e.g., percentage within a desired range), and/or intensity. In some cases, the workout summary may enable the user to adjust/correct the captured data; for example, a user may trim off time spent during a warm-up/cool-down, correct estimated distance with an actual distance, etc.

Figure 3:
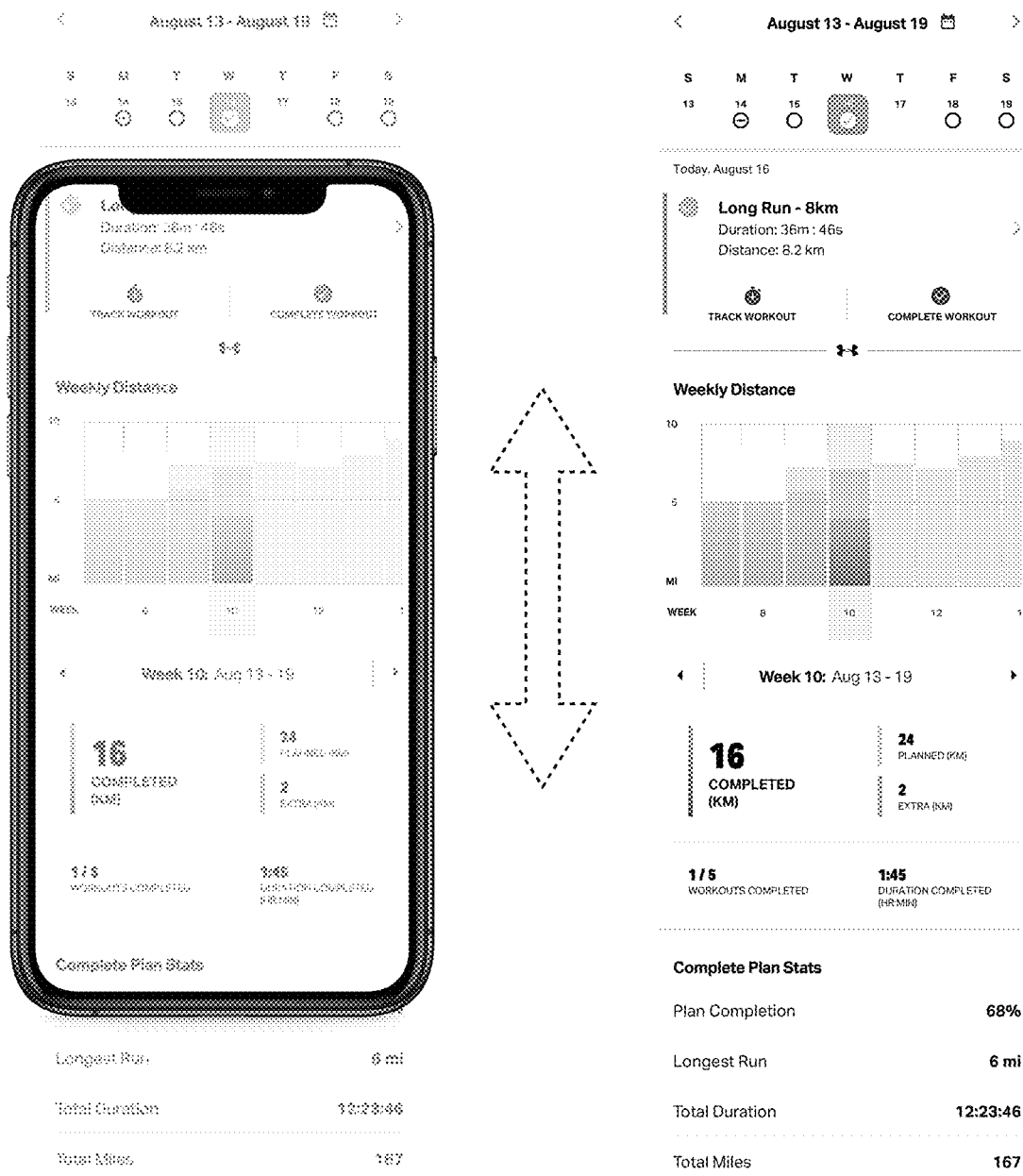
FIG. 3 is an exemplary screen shot of a user's historic workout summary, consistent with the various principles described herein.

Thereafter, the wearable updates the coordinating device with the workout data record. The coordinating device tracks the user's training plan progress. FIG. 3 illustrates an exemplary screen shot of a user's historic workout summary, consistent with the various principles described herein. As shown, the exemplary coordinating smart phone can display collected metrics that have been matched to completed workouts of the training plan. The metrics may update over time as more accurate values become available. For example, initially the workout may be shown with the default distance of 8.0 km corresponding to the suggested workout. However, the distance may be updated with higher confidence metrics a little later when the smart watch and/or smart shoes pair with the smart phone (e.g., 8.0 km updated to 8.2 km, duration updated to 36 min. 42 sec., etc.).

Various embodiments of the present disclosure additionally provide the coordinating device's records back to the fitness tracking system so as to e.g., provide back-up recordation as well as better recommendations. As previously alluded to, the fitness tracking system can periodically re-assess the user's workout progress to offer updated suggested workouts, training plan re-selection, and/or improved coaching based on peer performance data. In one such variant, the user's progress on their associated training plan may be re-assessed every few weeks, based on the user's actual workout results (actual pace, distance, etc.) In some cases, there may be multiple re-assessment types with different schedules; for example, a first set of re-assessments may be scheduled bi-weekly to adjust pace, a second set of re-assessments may run weekly and adjust mileage, etc.

Network Architecture

Figure 4:
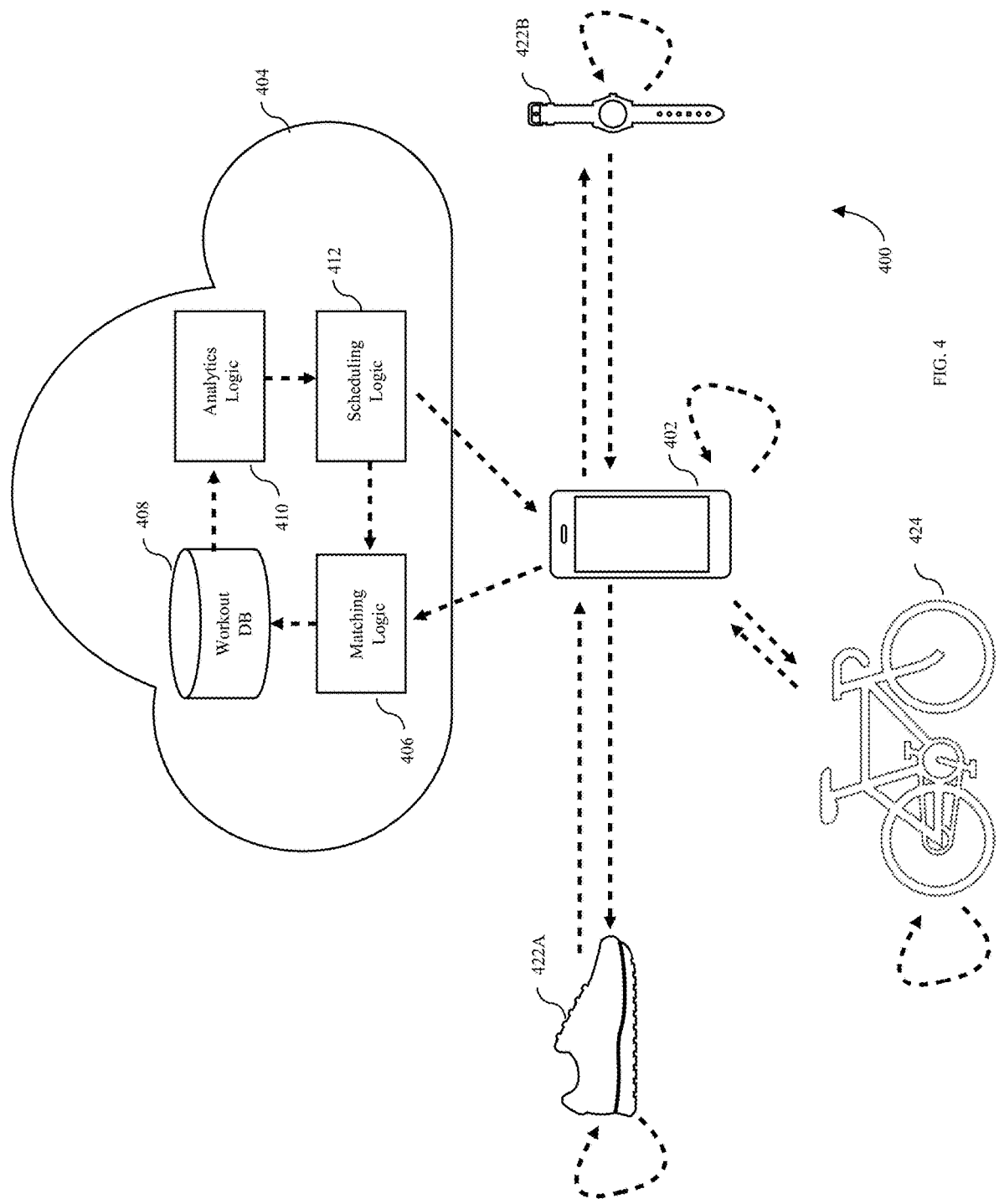
FIG. 4 is a logical block diagram of an exemplary network architecture configured to suggest (notify), track, and/or log workouts in accordance with the various principles described herein.

Referring now to FIG. 4, an exemplary network architecture 400 configured to suggest (notify), track, and/or log workouts in accordance with a training plan is shown. As illustrated, the system 400 includes one or more personal devices 402, 422, 424 in communication with a fitness tracking network 404. In one exemplary embodiment, the fitness tracking network 404 may include matching and/or reconciliation logic 406 in communication with a user workout history database 408; the user workout history database 408 may additionally be coupled to analytics logic 410 and scheduling logic 412.

As shown, a coordinating device 402 may be in communication with a community of personal devices. In one exemplary embodiment, the community of personal devices may include one or more wearable devices 422. For example, in the illustrated network, the wearable devices include a smart shoe 422A and a smart watch 422B. Other common examples of wearable devices include without limitation: pedometers, headphones, smart clothing, smart jewelry, smart glasses (and other head mounted displays), implantable devices, etc.

More generally, artisans of ordinary skill in the related arts will readily appreciate that the various principles described herein are not limited to "wearable" devices. As used herein, the term "personal device" refers to a set of devices associated with a user. The association may be permanent, temporary, or some variant thereof. As but one such example, a smart phone 402 may identify nearby smart exercise equipment and push workouts thereto and/or receive workout data therefrom. Consider a communal smart stationary bicycle 424 provided as part of a weekly cycling class membership at a user's gym. The user's smart phone 402 may notify the user when it is time to go to cycling class. The smart bicycle 424 may associate (pair) with the smart phone 402 (e.g., a "reserved seat in class") and also collect the user's workout metrics during cycling class (e.g., distance, time, cadence, calories burned, etc.) Similar techniques may be used for treadmills, rowing machines, weightlifting machines, and/or any other so-enabled exercise equipment.

As used herein, the terms "coordinate", "coordinator", and "coordinating" refers to logical entities that control and manage data within a community of personal devices corresponding to a user. In one embodiment, the community may include one or more "coordinator" devices that distribute workout notifications to one or more "coordinated" devices and receive workout data from the coordinated devices.

The user's community of devices may have many different functionalities that satisfy different useful niches with regard to personal health and fitness tracking. Common examples of functionality that may be offered by different personal devices may include, without limitation: education and/or motivation, training plan selection, suggested workout modification, workout data analytics, workout scheduling, workout notifications, workout input and/or feedback, workout metrics capture, and/or any related workout management tools. For example, a smart phone may enable a user to self-educate and/or browse through training plans; additionally, the smart phone may coordinate suggested workout delivery among a community of wearables. In one illustrative example, workout notifications as well as user input (accept, skip, snooze) may be handled via a smart watch whereas workout metrics may be captured via a smart shoe and/or smart stationary cycle.

Referring back to FIG. 4, the fitness tracking network 404 may include one or more wired and/or wireless, private and/or public network, including but not limited to, e.g., the Internet. The fitness tracking network 404 may include a wireless local area network (WLAN), wireless wide area network (WWAN), wired network, or any other suitable communication channel. Accordingly, each of: (i) matching and/or reconciliation logic 406, (ii) user workout history database 408, (iii) analytics logic 410 and (iv) scheduling logic 412 are configured with appropriate networking communication interfaces. One common example of wired communication is Ethernet; other common examples of communication interfaces may include, but are not limited to, near field communication (NFC), Bluetooth, Wi-Fi, 4G or 5G LTE. It is further appreciated that various gateways, routers, switches, base stations, etc. may be involved in facilitating and forwarding communication between the foregoing devices. It is noted that the fitness tracking network 404 may be itself, composed of several networks, such that the described components are distributed in various ones thereof. In alternative embodiments, the fitness tracking network 404 may include a series of devices communicating within software via application programming interfaces (APIs).

In one exemplary embodiment, the coordinating device 402 is the central distribution point for the community of personal devices (e.g., smart phone 402, smart shoe 422A, smart watch 422B, smart equipment 424). For example, the coordinating device 402 may communicate via a cellular (e.g., 4G, 5G) or wireless local area network (e.g., Wi-Fi) connection to the fitness tracking network 404; the community of devices may use a personal area network (e.g., Bluetooth, etc.) to transact data therebetween.

While the illustrated community of personal devices is depicted as a "star" network topology that is controlled by the coordinating device 402, artisans of ordinary skill in the related arts given the contents of the present disclosure will readily appreciate that other network topologies may be substituted with equal success, the foregoing being purely illustrative. Other common examples of network topologies include without limitation: peer-to-peer, tree, daisy-chain, ring, bus, mesh, or some hybrid thereof.

Moreover, while the illustrated implementation has a single coordinating device, other implementations may enable multiple coordinating devices. For instance, a community may have both: (i) a smart phone coordinator, and (ii) a smart watch coordinator, each coordinator being able to directly connect to the fitness tracking network 404 via an independent network connection, etc. Multiple coordinating devices may provide additional redundancy, functionality, and/or network reliability.

Referring back to FIG. 4, the coordinating device 402 collects data records corresponding to the user's workouts and provides the collected data records to matching and/or reconciliation logic 406. As previously alluded to, the user's workout data records may be generated by any number of different devices within the user's community of personal devices; moreover, the different sources of data records may have varying levels of integration, functionality, and/or capability. Tightly integrated devices may report user data records in exactly the format that is expected by the fitness tracking network 404; loosely integrated devices may incorrectly implement application programming interface (API) calls, incorrectly report data, estimate (rather than measure) data, and/or introduce other sources of uncertainty.

As used herein, the terms "match", and "matching" refer to the processes of identifying where and how data should be associated to other data structures. For example, unstructured captured data (e.g., a step count devoid of workout context) may be matched to a completed workout data records, which may be matched to a corresponding suggested workout.

As used herein, the terms "reconcile", and "reconciling" refer to the processes of ensuring that multiple independent data structures that purport to measure the same (or closely related) data are in agreement. For example, two contradictory step counts (e.g., stored at a coordinating device and a fitness tracking system) are reconciled when the contradictory step counts are resolved to a single step count for the workout data record. In another such example, related metrics e.g., distance, average stride length, and step counts are reconciled when the related metrics are consistently resolved for the workout data record (e.g., distance equals step count multiplied by average stride length, etc.) Various other reconciliations would be readily appreciated by artisans of ordinary skill in the related arts, given the contents of the present disclosure.

In one exemplary embodiment, the matching and/or reconciliation logic 406 parses through the provided data records and matches the data records to one or more suggested workouts that were provided via the scheduling logic 412. For example, a tightly integrated smart shoe 422A may provide step count data records that are uniquely associated with a suggested workout identifier, whereas a generic smart watch 422B may provide an approximate step count and heart rate data records which are generally proximate to (but not directly linked to) the suggested workout identifier. In this situation, the matching logic 406 may retrieve the step count associated with the smart shoe 422A (ignoring the approximate step count provided by the smart watch 422B) and augment the workout data records with the heart rate data records from the smart watch 422B.

In one exemplary embodiment, the matching and/or reconciliation logic 406 may use hierarchical logic to determine which data records should be used and/or preferentially weighted. In some cases, the hierarchical weighting may be static; for example, a smart shoe may be preferred for step data, a smart watch may be preferred for heart rate data, and a smart phone may be preferred for GPS location data. In other variants, the hierarchal weighting may be configured e.g., by the user, coordinating device, and/or fitness tracking system. For example, a user may prefer to use the step count provided by a smart watch, rather than a smart phone, etc. Similarly, a coordinating device or fitness tracking system may preferentially prefer data from certain coordinated devices due to e.g., manufacturing quality, business considerations, and/or other device specific considerations.

In some variants, the matching and/or reconciliation logic 406 may make inferences from data records, even where the data record is not directly used as a workout data record. Revisiting the aforementioned example, a less accurate step count for a smart watch 422B may be used to time align with a more accurate step count from a smart shoe 422A. In this manner, the smart watch's other measurements (e.g., heart rate, location, etc.) can be definitively associated with a suggested workout.

More generally, artisans of ordinary skill in the related arts will readily appreciate that virtually any scheme for matching and/or reconciling different workout data may be substituted with equal success. Such schemes may consider e.g., user configuration, intrinsic device capability, corroborating data captured via other devices, similar and/or related types of data (e.g., step count, pace, and/or time have mathematical relationships with distance, etc.)

Referring back to FIG. 4, the user workout history database 408 stores a plurality of user data records and their corresponding workout data records. As used herein, the term "database" refers to a structured set of data records held within a non-transitory computer-readable medium and/or the mechanisms used to e.g., add, remove, modify, and/or query and retrieve the stored data records. The term "data record" refers to a collection of data structures that represent an association, grouping, organization, or other collection of information; common examples of data structures include without limitation: numbers (integers, floating point), values (Booleans, enumerations), characters, strings, arrays (1D, 2D, N×D, etc.), lists, hash tables, etc. For example, a database may be queried for one or more data records that satisfy a particular condition; e.g., containing a particular string, value, etc.

In one exemplary embodiment, each workout data record may include detailed information with regard to e.g., location of exercise, date/time of exercise, scheduled date/time of future exercise, type and/or number of exercise, frequency of exercise, exerted muscle groups, duration of exertion, intensity of exertion, absolute load, relative load, range of movement, repetition, recovery time, fatigue, dynamic feedback/user response, frequency of revision, revision success/failure, and/or any number of other workout specific parameters. More generally, artisans of ordinary skill in the related arts given the contents of the present disclosure, will readily appreciate that virtually any data regarding either the individual users and/or their specific workout history can be stored and/or analyzed for e.g., matching and/or reconciliation, analytics, assessments, etc.

Referring back to FIG. 4, workout data records may be analyzed by an analytics logic 410 to recommend an initial training plan and/or recommend changing to another training plan (re-assessments) based on actual tracked progress. As a brief aside, humans widely vary in their baseline physiology and psychology; these differences affect workout efficacy; for example, two people of different height, weight, fitness, musculature, and mental outlook may run a 10 K with different levels of exertion and performance progression. As a practical matter, the wide variation in human physiology and psychology can result in widely different rates of performance progression. Providing an accurate initial assessment ensures that a user is not initially underwhelmed or overwhelmed by their training plan. Similarly, providing accurate re-assessments and recommending new training plans ensures that deviations from the user's initially selected training plan due to differences in performance progression keeps users engaged and motivated in their personal fitness journey, resulting in much better outcomes.

In one embodiment of the present disclosure, workout data records may be analyzed for similarity to models of performance progression. In some cases, the models of performance progression may be taken from existing physiological modeling. In other cases, the models of performance progression may be crowdsourced from a community of users. In one such variant, the models of performance progression may be based on users having similar physiological and/or psychological performance. For example, as described in co-owned, co-pending, U.S. patent application Ser. No. 16/588,199 filed Sep. 30, 2019 and entitled "METHODS AND APPARATUS FOR COACHING BASED ON WORKOUT HISTORY", incorporated herein by reference in its entirety, workout data for a population of different individuals may be analyzed to identify groups of similarly performing individuals. Each group of individuals may be analyzed to generate an expected profile that approximates the physiological and/or psychological traits of the group. A user's training plan can be initially selected and/or dynamically re-selected, based on their closest expected profile.

Once selected, the initial training plan and/or training plan updates can be delivered to the user's coordinating device via scheduling logic 412. Notably, training plans and/or training plan updates may not always warrant delivery. For example, a user that has performed according to expected performance progression may not require training plan re-selection/updates. Similarly, a user that has recently had an update may need time to settle into the new routine (to prevent churn) because their performance may not be representative of their actual capabilities. In still another example, a user that set a training plan based on a special event (e.g., a race event, etc.) may be unable to finish the event distance regardless of training plan re-selection and/or workout modifications. Under such scenarios, the scheduling logic may notify the user that their goal is unattainable within the set time frame or other parameters (this may allow the user to e.g., timely file for refunds of entry fees, etc.)

In the illustrated embodiment, the aforementioned entities are separate and distinct from one another; however, in other variants, the entities may be incorporated in part or in whole with various other ones of the foregoing. For example, workout data records that have been logged (or scheduled) at the coordinated devices 422A, 422B, 424 may be stored locally until e.g., reconciled with the coordinating device 402 and/or database 408 (or vice versa). Additionally, or in the alternative, training plans (in whole or in part) may be stored at the scheduling logic 412 and portions may be made accessible to particular devices 402 when queried and/or locally cached. For example, suggested workouts (rather than the training plan) may be delivered to the user's coordinating device. Thereafter the coordinating device can manage distribution of suggested workouts within the user's community of personal devices. Any combination of the foregoing configurations may be utilized with equal success.

While the illustrated example is presented in the context of running, other athletic activities may be substituted, the foregoing being purely illustrative. Common examples include without limitation: cycling, swimming, weightlifting, athletic activities, etc. More broadly, the techniques described herein may be applied to any health and/or fitness tracking activity. Common examples of other tracked activities include e.g., nutrition tracking, sleep tracking, etc.

Methods

FIG. 5A is a logical flow diagram of an exemplary method 500 for suggesting workouts to a user, in accordance with the various principles described herein. In one variant, the method 500 additionally includes re-assessing the training plan based on actual user workout data At step 502 of the method 500, workout data records and/or user input are collected. In one embodiment, user data may be obtained from a variety of data sources including without limitation: personal devices (see step 512 of FIG. 5B, discussed in greater detail infra), $3^{rd}$ party databases (social networks, medical and/or health/fitness databases), associated health or athletic professionals (e.g., physicians, nutritionists, personal trainers, coaches, etc.) and/or peer activity (teammates, family members, etc.) In one such embodiment, the user may be prompted to identify (and/or authorize) access to external data sources. For instance, an athlete may grant training plan access (read-only, write-only, read-write, etc.) to their coach; in this manner, the coach can coordinate workouts across a sports team. In another example, a fitness tracking service may have affiliates and/or partnered relationships with external data sources which make user information available as part of a service contract, etc.

While the foregoing techniques envision workouts that are customized for each individual user based on user-specific data and their associated training plan, artisans of ordinary skill in the related arts given the contents of the present disclosure will readily appreciate that other methods for identifying suitable training plans that are not based on user-specific information may be substituted with equal success. For example, some training plans may be interpolated and/or extrapolated from non-user specific sources e.g., popular training plans, historically successful training plans, expert knowledge, etc. Similarly, some "group-specific" training plans may be implemented within a team setting (e.g., a sports team, law enforcement/military unit, etc.)

At step 504 of the method 500, the collected data is analyzed to identify one or more training plans for the user. In one exemplary embodiment, the collected user information (e.g., user history workout data records, user solicited input, and/or other information) may be compared against different training plan progressions. For example, a user's desired outcome (run a 10 K), scheduling requirements (within 10 weeks), and/or previous workout history (e.g., previously 5 K workout data records), can be compared against different progressions associated with training plans (e.g., an "Intermediate 10 K" training plan has an acceptable duration (12-32 weeks), and is suitable for people that have previously completed running workouts). In some cases, several suitable training plans may be identified that would satisfy the user's intended performance progression; the suitable training plans may be provided to the user for further winnowing (see step 514 of FIG. 5B, discussed in greater detail infra). In some such implementations, the user may additionally provide feedback regarding the recommended training plan. In this manner, the user can iteratively receive better training plans that best fit their personal fitness journey.

While the foregoing discussion is presented in the context of an iterative selection process, artisans of ordinary skill in the related arts given the contents of the present disclosure, will readily appreciate that virtually any data analysis technique may be used to identify training plans based on the collected data. In one embodiment, data analysis may include fitting algorithms which estimate a likely user performance progression and compare the estimated performance progression against different training plan progressions for "fit." Common examples of fitting algorithms include without limitation e.g., linear fit, least squares fit, regression analysis, polynomial fit, etc. In another variant, data analytics may incorporate performance progression information from a group of individuals having similar physiological and/or psychological parameters, such as was described in co-owned, co-pending, U.S. patent application Ser. No. 16/588,199 filed Sep. 30, 2019 and entitled "METHODS AND APPARATUS FOR COACHING BASED ON WORKOUT HISTORY", incorporated supra.

As used herein, the terms "analyze" and "analysis" refers to any technique, method, process, algorithm, and/or system that examines a data set to extract relationships from the data set. Analysis may be manual (e.g., entry based on human analysis), automatic (machine learning), or a hybrid thereof (e.g., software identification with human acknowledgement, etc.) More generally, artisans of ordinary skill in the related arts given the contents of the present disclosure, will readily appreciate that virtually any scheme for data analysis may be substituted with equal success the following being purely illustrative. Data analytics may be based on structured and/or unstructured data, and may include e.g., cleansing, organization, algorithmic processing, statistical processing, artificial intelligence, machine learning, and/or any "big data" processing (e.g., data structures and processing that exceed the capabilities of a single processor/memory.)

Once a training plan is selected, suggested workouts can be scheduled in accordance with the training plan. In one exemplary embodiment, a fitness tracking system suggests workouts and provides the suggested workouts to the coordinating device. In other embodiments, the suggested workouts can be generated by the coordinating device based on a local copy of the selected training plan. The coordinating device thereafter controls and manages data for the user's community of personal devices (see e.g., FIG. 5B discussed in greater detail infra.)

When the user completes the workout, any workout data records are matched to suggested workout data records at step 506 of the method 500. In one embodiment, the matching is based on a unique workout identifier associated with its corresponding suggested workout. For instance, suggested workout notifications may include a unique workout identifier; subsequently received workout data records that have the same unique workout identifier are "matched" together.

As previously alluded to, suggested workouts may not always be performed immediately. Additionally, multiple wearables may collect data regarding the same workout; for example, a smart shoe may capture steps at the same time as a smart watch. In other words, the flexibility inherent to wearable devices may be more convenient for the user but can introduce ambiguity in terms of data analysis. Consequently, various embodiments of the present disclosure may further need to reconcile captured data across multiple workout data records with suggested workouts.

In one exemplary embodiment, the matching and/or reconciliation techniques may be multi-variate in nature and/or associated with some degree of confidence. As but one illustrative example, a smart watch may record that a suggested workout was accepted at a specific date and time; the smart watch may match the suggested workout to a measured distance of 8.3 km via GPS and 5,832 steps based on arm swings. Concurrently, a set of smart shoes may have also matched 6,123 steps for the same suggested workout identifier, but at a different time and date (e.g., due to different time bases). The workout data records may be reconciled to reflect an 8.3 km run with the smart watch's date and time stamp and the smart shoe's 6,123 steps. In this manner, the most accurate sources of workout data can be recorded for the workout. In some implementations, the reconciled data records may be kept, such that a user can review and manually correct ambiguities in reconciled workout data records.

A wide range of matching and/or reconciliation techniques may be used consistent with the various principles described herein. As previously noted, matching and/or reconciliation logic may be based on unique identifiers; for example, workout data records associated with a suggested workout may use a common unique identifier. In one such variant, matching and/or reconciliation logic may also be associated with confidence levels so as to resolve ambiguities between contradictory data records. Confidence levels may be predefined, or dynamically set based on a variety of considerations (e.g., device accuracy, device history, correlation with related data, etc.) In some variants, matching and/or reconciliation logic may incorporate user input so as to unambiguously reconcile contradictory data records.

More sophisticated matching and/or reconciling may analyze a plurality of different data records via multi-variate matching algorithms. Multi-variate logic may infer matches/reconciliations even where no common unique identifier is present; this may be particularly helpful when incorporating data records from personal devices that are unable and/or restricted from directly communicating with the community of personal devices. For example, legacy devices may be unable to interface with the coordinating device but may provide APIs for general access via the Internet (e.g., accessible via the fitness tracking network). As but another example, a smart shoe and a smart watch may both concurrently capture different workout data that are later augmented and/or combined into a single data record.

In other such examples, peer devices (e.g., a running partner's wearable) may provide workout data records that may or may not correlate with the user's workout activity. The peer data record may be used to augment the user's workout data records, if the peer's data record is sufficiently similar. For instance, two running partners may run a similar distance in a similar time (within matching tolerances) even though they have different stride lengths and/or step counts. Still other multi-variate matching algorithms may be substituted by artisans of ordinary skill in the related arts, the foregoing being purely illustrative of the various principles described herein.

Common examples of information that may be useful for matching and/or reconciling may include e.g.,: location of exercise, date/time of exercise, exercise distance, exercise duration, capture device, estimated calories expended, environmental conditions (weather, temperature, etc.), heart rate, fatigue, cadence, stride length, activity type, pace/velocity, and/or previous confidence based on previous successful matching/reconciliations.

At step 508 of the method 500, the user's training plan progression is updated based on workout data records. In one exemplary embodiment, workout data records may be re-assessed to recommend training plan re-selection and/or suggested workout modifications based on actual tracked progress. In one such variant, workout data records may be analyzed for physiological progress. For example, a user's pace and distance may be compared to expected models of performance progression. In other such variants, workout data records may be analyzed for psychological behavior. For example, a user that continually misses workouts may be flagged for counseling or other psychological assistance (e.g., motivational media, question-response "bot" type counseling, and/or human counseling)

In one embodiment, the re-assessments may be scheduled periodically (or substantially periodically, subject to user considerations). In some such variants, different types of re-assessments may have different time intervals. For example, pace re-assessments may occur on a different frequency from distance re-assessments. Some variants may allow a user to shift their assessments around other scheduling constraints.

In some embodiments, re-assessments may be conditionally triggered. As but one such example, re-assessments may be triggered whenever a threshold condition is exceeded/not met (e.g., the user has a string of unexplained skips). In another such example, re-assessments may be triggered by scheduled events (e.g., the user gets a re-assessment a few days prior to a race event). Still other conditional re-assessments may be readily substituted by artisans of ordinary skill given the contents of the present disclosure, the foregoing being purely illustrative.

As used herein, the term "conditional" refers to any action or event that is subject to one or more logical conditions or requirements being met. Common examples of conditional rules include e.g., "if-then", "only-if-then", "do-until", "perform-while-true", "case(s)", and/or other Boolean logic. While the conditional logic is described herein, artisans of ordinary skill in the related arts given the contents of the present disclosure will readily appreciate that non-Boolean based rules may be substituted for conditional rules with equal success. Common examples of non-Boolean rules include without limitation: machine learned rules, pattern-based rules, predictive rules, weighted rules, "fuzzy" logic, and/or other techniques.

Advantageously, there may be situations where a user may not be aware of how their personal habits may interfere with regular workouts. For example, a user that has a morning workout schedule may not realize that sleeping late at night or eating a large dinner has a substantial impact on their morning routine. To these ends, re-assessment logic may consider not only the user's actual workout data records, but also a variety of other factors including without limitation: diet, sleep schedule, work schedule, other activities and/or obligations, peer schedules, etc. In some cases, re-assessment logic may greatly improve workout retention merely by identifying that workouts should be shifted in time, moved to different days, or performed ahead of schedule to avoid skips.

While the foregoing discussion is presented in the context of a central fitness tracking system (such as would be provided by a health and fitness tracking service), artisans of ordinary skill in the related arts given the contents of the present disclosure will readily appreciate that other implementations may be substituted with equal success the foregoing being purely illustrative. For example, in other implementations, a user's own server, laptop, smart phone, or other personal device may perform the method 500 of FIG. 5A.

FIG. 5B is a logical flow diagram of an exemplary method 510 for coordinating delivery of suggested workouts to a user, in accordance with the various principles described herein.

At step 512 of the method 510, user input is obtained for training plan selection and/or suggested workout modifications. For example, a user provides input to customize suggested workouts for their selected training plan. In one embodiment, user input can be directly solicited from the user based on subjective and/or objective questions regarding e.g., the user's current desired goals, the user's long term aspirational goals, starting physiological and/or psychological characteristics, other fitness parameters (sleep, nutrition), external scheduling considerations, available wearables and/or other equipment, previous exercise history, medical considerations, and/or any other information useful for navigating a user's personal fitness journey.

In one embodiment, the user input may be captured at a personal device and provided to a fitness tracking system for analysis and training plan recommendation. In other embodiments, the fitness tracking system may provide a set of training plans to a user's personal device, for the user to browse, accept, reject, modify, etc. In still other embodiments, a user may create a user account/login to a user account at a fitness tracking service provider via a web portal; the user's account may include user input as part of the onboarding process. Various other schemes for collecting user input may be readily substituted by artisans of ordinary skill in the related arts, given the contents of the present disclosure.

More generally, a variety of different inputs may be considered to customize the user's suggested workouts associated training plans. While the foregoing examples are based on user-specific considerations, other embodiments may consider non-user specific considerations. As but one such example, group-specific implementations may attempt to ensure that a group of users progress together (such as is common with team sports). Similarly, event-specific implementations may attempt to ensure that a user's performance progression meets specific event milestones (e.g., qualifying day, race day, etc.) In yet another example, business and/or monetary incentives may be considered; for example, a gym may incentivize new memberships by offering reduced membership rates for members that start a training plan (and stick to their workout routines). Still other implementations may be substituted by artisans of ordinary skill in the related arts, given the contents of the present disclosure, the foregoing being purely illustrative.

Referring back to FIG. 5B, a training plan and/or suggested workouts based on the training plan are obtained by the coordinating device (step 514 of the method 510). In some cases, the training plan and/or suggested workouts may require further user feedback iterations (e.g., via step 512 of the method 510, and/or steps 502, 504 of the method 500, described supra). Otherwise the training plan and/or suggested workouts may be provided to the coordinating device to manage and/or control suggested workouts within a community of personal devices corresponding to a user (e.g., via step 516 of the method 510, described infra.)

In one embodiment, the coordinating device generates suggested workouts based on the selected training plan. In another embodiment, the coordinating device receives suggested workouts from the fitness tracking system (based on the selected training plan). Other embodiments may receive suggested workout notifications from devices not associated with the user but otherwise permitted to interact therewith. For example, a personal trainer's smart stopwatch (if appropriately authorized) may push a suggested workout, etc. Still other implementations may be substituted by artisans of ordinary skill in the related arts given the contents of the present disclosure, the foregoing being purely illustrative.

In one embodiment, the coordinating device may receive a suggested workout notification from a coordinated device. As but one such example, a pro-active user may know of their scheduled workout and initiate a workout ahead of schedule via their smart watch (which is normally controlled by their smart phone). As described in greater detail hereinafter (see e.g., step 518), the smart phone (coordinating device) may match the user-initiated suggested workout (e.g., initiated at the smart watch) with a subsequently suggested workout from a fitness server. The matching may be based on a time window, common rule, or other heuristic (e.g., a user-initiated morning workout can be automatically matched to server-initiated afternoon workouts, etc.) In other words, the exemplary coordinating device may ensure that pushed suggested workouts have not been pre-emptively completed by the user ahead of time.

Referring back to step 514, in one embodiment, the suggested workout distribution is a selectable preference that can be set by the user. In one such variant, the coordinating device may display the notification itself (as an "in-app" notification) or push the notification to a currently paired wearable depending on user preferences. For example, the user may prefer to receive suggested workout notifications via the coordinating device (e.g., via an in-app notification); alternatively, the user may select to receive suggested workout notifications via a coordinated device (such as a wearable).

In one such variant, the coordinating device may distribute suggested workouts to personal devices based on availability. Wearable availability may be determined by the wearable itself and/or by the coordinating device. In one such implementation, a coordinating device may broadcast notifications to all paired wearables, each wearable is independently responsible for managing its suggested workout notification. For example, a smart phone broadcasts a suggested workout to a smart watch; the smart watch checks a heart rate to infer the presence of a user. If the smart watch is being worn (e.g., heart rate is present), then the smart watch provides the workout notification; otherwise, the notification is ignored (or postponed until a heart rate is detected). In other implementations, the coordinating device may determine wearable availability; for example, the smart phone may have an operating system (OS) application programming interface (API) that provides device availability information to local applications; e.g., the OS may manage a personal area network (PAN) and provide a registry of nearby wearables to the local fitness tracking application.

Additionally, the coordinating device may consider hierarchical priority when distributing suggested workouts to personal devices. For example, some embodiments may limit distribution based on a hierarchical priority so as to minimize unnecessary tracking. As but one example, a suggested workout run may only be distributed to smart shoes for step count, whereas a suggested bike workout may be distributed to a smart watch for location data, etc. In other embodiments, the hierarchical priority may be used to maximize usability across multiple devices. As but one example, a suggested workout run may be preferentially distributed to a smart phone and/or a smart watch, depending on user interface (UI) requirements. Other common examples of considerations that can benefit from hierarchical prioritization include without limitation: accuracy, power consumption, performance, redundancy, convenience, etc.

Notably, a single suggested workout data record may be propagated to multiple personal devices and/or a single workout data record may match to multiple different suggested workouts. In other words, suggested workouts may match to workouts on a one-to-one, one-to-many, many-to-one, many-to-many, etc. For example, a single run may be concurrently tracked by both a smart watch and a smart shoe (one-to-many). Similarly, a multi-staged workout (run, cycle, swim) may be suggested in multiple stages, but completed in one shot (many-to-one).

Additionally, the suggested workout notification and workout data record may not perfectly align in time or captured metrics. For example, a user may start running, and realize only later that they did not start their step count. Similarly, a user may end a workout but forget to stop tracking their heart rate. Matching between unknown time alignments and/or different metrics can be a difficult problem to solve (also referred to as "boundary adjustment" and/or "workout trimming"). To these ends, some personal devices may provide multiple workout data records of different confidence levels corresponding to the same suggested workout; e.g., there may be a high confidence workout data record, and a lower confidence pre-workout and post-workout workout data record. The fitness tracking server and/or user device can use multi-variate matching logic to appropriately match and/or reconcile different data records. In one exemplary implementation, boundary adjustment is performed prior to matching so as to reduce matching complexity. In other implementations, boundary adjustment may use matching feedback e.g., to improve the captured workout data. Various other combinations and/or hybrids of trimming may be substituted by artisans of ordinary skill in the related arts.

More generally, various embodiments of the present disclosure decouple suggesting workouts from tracking workouts. In an illustrative example, a runner could select a training plan on their smart phone, the smart phone pushes notifications to any available wearables, and the user tracks their workout completion with their available wearables (e.g., smart watch, smart shoe). Functionally, the different devices need only handle what they were designed for e.g., the wearables can handle the aggressive workout usage, while the smart phone can handle more complex user experience (UX).

In one embodiment, the suggested workout data record may include e.g., a unique suggested workout identifier, a device specific identifier (e.g., MAC address, etc.). In some embodiments, the suggested workout data record may additionally include goal data records and/or performance metrics e.g., suggested start time, suggested start date, suggested geofence start/end location, goal distance, goal duration, goal pace, goal cadence, goal calories, goal steps, target heart rate, and/or any other relevant suggested workout parameters.

As previously alluded to, there are some situations where the coordinating device may directly notify the user of suggested workouts, and allow the user to start tracking a workout, snooze a workout for later, and/or skip a workout. In other words, some embodiments of the present disclosure may allow a personal device (e.g., a smart phone) to coordinate delivery of suggested workouts to a user, as well as track the suggested workout progress. These functions are described in greater detail infra (see discussion of FIG. 5C).

Referring now to step 518 of the method 510, the coordinating device may return completion status and/or data records to the fitness tracking system. Common examples of completion status may include e.g., "completed", "percentage complete", "incomplete", "skipped", "snoozed". Common examples of data records may include e.g., time of start/end, date start/end, location start/end, distance, duration, average (and/or peak) pace, average (and/or peak) cadence, estimated calories, steps counted, average (and/or peak) heart rate, range (e.g., percentage within a desired range), intensity, etc. In some embodiments, the coordinating device may additionally identify when and how the data records were captured. For example, the coordinating device may include the corresponding unique suggested workout identifier and the source device identifier (e.g., the wearable or other personal device that generated the workout data record).

FIG. 5C is a logical flow diagram of an exemplary method 520 for tracking workouts via a personal device, in accordance with the various principles described herein.

At step 522 of the method 520, the coordinated device obtains a suggested workout. In some embodiments, the coordinated device may be pushed multiple suggested workouts. In one such example, a smart watch may load multiple stages of a multi-stage workout. As another example, a smart watch may pre-load all suggested workouts for a week.

In some situations, the personal device may fail to notify the user; for example, the wearable may not be currently worn, etc. In one exemplary embodiment, the personal device may re-attempt notification. For example, the personal device may use an exponential back-off and retry scheme (e.g., a retry at 15 minutes, 30 minutes, 1 hour, 2 hours, etc.). In other implementations, the re-attempt notification may be triggered by a conditional event (e.g., UI activity, presence detection, etc.) Still other variants may use e.g., redundant/fallback device notification, re-notification, and/or any other notification scheme.

In one embodiment, the coordinated device may pre-load target goals for the suggested workout. In one exemplary embodiment, the pre-loaded suggested workout data record stores the data structure locally at the coordinated device; in this matter, the coordinated device can reference the suggested workout data record and generate a workout data record without further assistance by e.g., the coordinating device, the fitness tracking server, etc.

In some embodiments, the coordinated device notifies the user and determines whether the user accepts the suggested workout (step 524 of the method 520). For example, a smart watch may notify the user of a suggested workout, and the user may start tracking the workout, snooze the workout for later, or skip the workout altogether. In other embodiments, the user's input is captured at the coordinating device and the coordinated device can begin tracking the workout. For example, a user may accept a workout on their smart phone, the smart phone notifies the user's smart shoes of an impending workout via the suggested workout data record. Thereafter, the smart shoe can start tracking the workout.

In one embodiment, the user can accept the suggested workout, snooze the suggested workout, or skip the suggested workout. Other implementations may allow a user to reschedule the workout to a later time or date, mark a workout as having been previously performed (but untracked), etc. More generally, any number of other user options may be substituted with equal success by artisans of ordinary skill in the related arts, given the contents of the present disclosure, the foregoing being purely illustrative.

In one embodiment, responsive to the user accepting a suggested workout, the coordinated device starts tracking the user's workout. Responsive to a user ending a workout, the coordinated device stops tracking the user's workout and writes a workout data record. In some variants, the coordinated device may have additional conditional requirements to identify the start and end of a workout; for example, a user may need to exceed a minimum pace to trigger the workout start. Similarly, a user that has fallen below a minimum pace for a set time may trigger the workout end.

Once the workout is completed, the captured workout metrics are stored in a workout data record. Common examples of captured workout metrics may include e.g., time of start/end, date start/end, location start/end, distance, duration, average (and/or peak) pace, average (and/or peak) cadence, estimated calories, steps counted, average (and/or peak) heart rate, range (e.g., percentage within a desired range), intensity, etc. In some embodiments, the coordinated device may additionally identify when and how the data records were captured. For example, the workout data record may include the corresponding unique suggested workout identifier and the source device identifier (e.g., the wearable or other personal device that generated the workout data record).

In one embodiment, the coordinated device may include a completion status to e.g., "completed", "percentage complete", "incomplete", etc. depending on the user's workout performance. In some embodiments, the completion status is based on captured workout metrics. In other embodiments, the completion status may reflect a user's intention. For instance, a suggested workout that is "accepted" by the user may automatically generate an intended completion data record. In such cases, the intended completion data record may include null data records and/or use default workout metrics (e.g., an untracked "8 km run" may be logged with the default distance of 8 km, etc.) In some variants, the intended completion data record may be later augmented with actual completion data and/or user input.

In still other embodiments, a suggested workout may only be "completed" if a minimum threshold was measured (e.g., a minimum distance was measured, etc.) regardless of whether or not the user has ended the suggested workout. A user that repeatedly accepts but does not complete workouts may be guided to a more suitable (realistic) training plan. Still other implementations may confirm completion and/or appropriate data with a user; e.g., a user may choose to "complete" an 8 km run, even if they only ran 5 km. Other implementations may allow a user to manually populate data for the workout data record and/or match wearable data against a workout data record.

Referring back to FIG. 5C, responsive to the user snoozing a suggested workout, the coordinated device sets a timer or an alarm to re-notify the user of their suggested workout. In some cases, the snooze option may have a few different delay options such as: snooze for one or more wait interval (s), snooze until a set time, etc. Subsequently thereafter, the snoozed suggested workout will remind the user; in some cases, a snoozed workout can be re-snoozed a number of times. In some cases, a snoozed workout requires either an affirmative accept or skip. In some cases, snoozed workouts may generate a completion status of "snoozed" and may additionally include information to identify why the workout was snoozed. Snooze information may be useful in subsequent workout analysis to identify conditions which are most conducive to workout scheduling. For example, a user that consistently snoozes morning workouts may have a better experience working out in the afternoon.

In one embodiment, responsive to the user skipping a suggested workout, the coordinated device generates a workout data record indicating "skipped" in the completion status.

At step 526 of the method 520, the coordinated device returns completion status and/or data records. In one embodiment, the coordinated device returns the completion status and/or data records to the coordinating device and/or the fitness tracking system. Still other coordinated devices may store their data records in a $3^{rd}$ party server which can be independently accessed via either the coordinating device or the fitness tracking system.

Apparatus

FIG. 6A is a logical block diagram of one exemplary server apparatus 600, useful in accordance with the various principles described herein. In one embodiment, the server apparatus 600 includes a processor 602, non-transitory computer-readable medium 604, and one or more network interfaces (e.g., a first network interface 606, and a second network interface 608).

The components of the exemplary server apparatus 600 are typically provided in a housing, cabinet or the like that is configured in a common manner for a server or related computing device. It is appreciated that the embodiment of the server 600 shown in FIG. 6A is only one exemplary embodiment of a server 600 for the fitness tracking system. As such, the exemplary embodiment of the server 600 described herein with reference to FIG. 6A is merely representative of any of various manners or configurations of servers or other data processing systems that are operative in the manner set forth herein.

The processing circuitry/logic 602 of the server 600 is operative, configured, and/or adapted to operate the server 600 including the features, functionality, characteristics and/or or the like as described herein. To this end, the processing circuit 602 is operably connected to all of the elements of the server 600 described below.

The processing circuitry/logic 602 of the host server is typically controlled by the program instructions contained within the memory 604. The program instructions 604 suggest workouts to a user as explained in further detail supra. The fitness tracking system at the server 600 is configured to communicate with and exchange data with the coordinator application running on a processor of a personal device. In addition to storing the instructions, the memory 604 may also store data for use by the fitness tracking program. As previously described, the data may include the workout data records, etc.

The network interfaces of the server 600 allow for communication with various devices using various means. In one particular embodiment, the network interface is bifurcated into a first network interface 606 for communicating with other server apparatuses and a second network interface 608 for communicating with a coordinating device. Other implementations may combine these functionalities into a single network interface, the foregoing being purely illustrative.

In one exemplary embodiment, the first network interface 606 is a wide area network port that allows for communications with remote computers over the Internet (e.g., external databases). The first network interface 606 may further include a local area network port that enables communication with any of various local computers housed in the same or nearby facility. In at least one embodiment, the local area network port is equipped with a Wi-Fi transceiver or other wireless communications device. Accordingly, it will be appreciated that communications with the server 600 may occur via wired communications or via the wireless communications. Communications may be accomplished using any of various known communications protocols.

In one exemplary embodiment, the second network interface 608 is a network port that allows for communications with a community of personal devices. The second network interface 608 may be configured to interface to a variety of different networking technologies consistent with consumer electronics. For example, the network port may communicate with a Wi-Fi network, cellular network, and/or Bluetooth devices.

In one exemplary embodiment, the server 600 is specifically configured to suggest workouts to a user, in accordance with the principles described above. In particular, the illustrated server apparatus 600 stores one or more computer-readable instructions that when executed e.g., collect workout data records and/or user input, analyze the workout data and/or user input to identify a training plan, match workout data records to suggested workout data records, and/or update the user's progression on their training plan.

FIG. 6B is a logical block diagram of one exemplary coordinator device 610, useful in accordance with the various principles described herein. In one embodiment, the coordinator device 610 includes a processor 612, non-transitory computer-readable medium 614, a first network interface 616, a user interface 618, and a second network interface 620.

The components of the exemplary coordinator device 610 are typically provided in a consumer electronics personal device such as a laptop or a smart phone. It is appreciated that the embodiment of the coordinator device 610 shown in FIG. 6B is only one exemplary embodiment of a coordinator device 610 for the fitness tracking system. As such, the exemplary embodiment of the coordinator device 610 described herein with reference to FIG. 6B is merely representative of any of various manners or configurations of personal devices that are operative in the manner set forth herein.

The processing circuitry/logic 612 of the coordinator device 610 is operative, configured, and/or adapted to operate the coordinator device 610 including the features, functionality, characteristics and/or the like as described herein. To this end, the processing circuit 612 is operably connected to all of the elements of the coordinator device 610 described below.

The processing circuitry/logic 612 of the coordinator device 610 is typically controlled by the program instructions contained within the memory 614. The program instructions 614 control/manage suggested workout delivery and tracking as explained in further detail supra. The coordinating application at the coordinator device 610 is configured to communicate with and exchange data with the fitness tracking system as well as any number of coordinated devices (described in greater detail hereinafter). In addition to storing the instructions, the memory 614 may also store data for use by the coordinating application. As previously described, the data may include the workout data records, etc.

The network interfaces of the coordinator device 610 allow for communication with various devices using various means. In one particular embodiment, the network interface is bifurcated into a first network interface 616 for communicating with the fitness tracking system and a second network interface 620 for communicating with a community of personal devices. Other implementations may combine these functionalities into a single network interface, the foregoing being purely illustrative.

In one exemplary embodiment, the first network interface 616 is a local area network port that allows for communications with computers over an Ethernet connection (e.g., the fitness tracking server 600). In another embodiment, the first network interface 616 is a cellular network port that allows for communications with a base station (that operates as a gateway to the broader Internet). In still another The first network interface 616 may be configured to interface to a variety of different networking technologies consistent with consumer electronics. For example, the network port may communicate with a Wi-Fi network, cellular network, and/or Bluetooth devices. Communications may be accomplished using any of various known communications protocols.

In one exemplary embodiment, the user interface 618 is the interface that allows for communication between the user and the device. Common examples of human-machine input devices include elements such as e.g., touch screens, microphones, speakers, keypads, mice, buttons, and/or any number of other human input devices.

In one exemplary embodiment, the second network interface 620 is a network port that allows for communications with a community of personal devices. The second network interface 620 may be configured to interface to a variety of different networking technologies consistent with consumer electronics. For example, the network port may communicate with a Wi-Fi network, cellular network, and/or Bluetooth devices.

In one exemplary embodiment, the coordinator device 610 is specifically configured to manage and control suggested workouts distribution, in accordance with the principles described above. In particular, the illustrated coordinator device 610 stores one or more computer-readable instructions that when executed e.g., obtain training plans, manage and control suggested workouts, track the user's workout metrics (if necessary), and return completion status and/or data records.

FIG. 6C is a logical block diagram of one exemplary personal device 630, useful in accordance with the various principles described herein. In one embodiment, the personal device 630 includes a processor 632, non-transitory computer-readable medium 634, a network interface 636, user interface 638, and sensors 640.

The components of the exemplary personal device 630 are typically provided in a wearable form factor that is configured for everyday use and/or ruggedization. Examples of wearables include e.g., smart watches, smart shoes, pedometers, headphones, smart clothing, smart jewelry, smart glasses (and other head mounted displays), implantable devices, etc. It is appreciated that the embodiment of the personal device 630 shown in FIG. 6C is only one exemplary embodiment of a personal device 630 for the fitness tracking system. As such, the exemplary embodiment of the personal device 630 described herein with reference to FIG. 6C is merely representative of any of various manners or configurations of personal devices that are operative in the manner set forth herein.

The processing circuitry/logic 632 of the personal device 630 is operative, configured, and/or adapted to operate the personal device 630 including the features, functionality, characteristics and/or the like as described herein. To this end, the processing circuit 632 is operably connected to all of the elements of the personal device 630 described below.

The processing circuitry/logic 632 of the personal device 630 is typically controlled by the program instructions contained within the memory 634. The program instructions 634 notify a user of a suggested workout and tracks workouts as explained in further detail supra. The personal device 630 is configured to communicate with and exchange data with the coordinator device. In addition to storing the instructions, the memory 634 may also store data for use by the wearable. As previously described, the data may include the workout data records, etc.

In one exemplary embodiment, the network interface 636 is a network port that allows for communications with a coordinator device. The network interface 636 may be configured to interface to a variety of different networking technologies consistent with consumer electronics. For example, the network port may communicate with a Wi-Fi network, cellular network, and/or Bluetooth devices.

In one exemplary embodiment, the user interface 638 is the interface that allows for unobtrusive communication between the user and the device via e.g., tactile, haptic, auditory, and/or time-insensitive visual interfaces. Common examples of such human-machine input devices include elements such as e.g., touch screens, microphones, speakers, buttons, rumble boxes, vibrators, and/or any number of other human input devices.

In one exemplary embodiment, the personal device 630 is specifically configured to track a user's workouts, in accordance with the principles described above. In particular, the illustrated personal device 630 stores one or more computer-readable instructions that when executed e.g., obtain suggested workouts, track the user's workout metrics, and return completion status and/or data records.

As used herein, the term "workout" refers to one or more activities performed by the user with measurable physiological and/or psychological impact. Examples of measurable physiological impacts may include without limitation e.g., cardiovascular strain, heart rate, caloric consumption, muscular exertion, fatigue, blood oxygenation, lactate production, blood occlusion, nervous system activation, temperature increase, sweat production, changes to form/body positioning (via video analysis), audible data (exhalations, foot strikes, etc.), and/or any other physical effect of exertion. Physiological data may be collected via one or more sensors 640 and/or the user device interface (e.g., buttons, touch screen, microphones, etc.). Common examples of sensors 640 include e.g., accelerometers, heart rate monitors, blood sensors, microphones, cameras, etc.

As used herein, "performance" and "performance metrics" refer to any set of workouts and/or predicted/expected physiological and/or psychological impacts for similar users based on e.g., physiology, psychology, fitness goals and/or any other relevant parameters. As used herein, the term "performance progression" is used to refer to a user's tolerable physiological and/or psychological impact as a function of time. For example, a user's physiological progression may be measured as a function of e.g., changes to heart rate as a function of distance run over multiple workouts, changes to maximum repetitions/sets of a load over multiple workouts, etc. Notably, while performance progression is generally measured physiologically, psychological measures may also have significant value. For example, some users may subjectively enjoy working out regardless of whether or not they improve their physiological performance. Also, a user's psychological impact may cause changes to motivation and/or outlook when they hit a physiological "plateau."

The above described system and method solves a technological problem common in industry practice related to coordinating suggested workout delivery within a community of personal devices. The above-described system and method improves the functioning of the computer/device by delivering suggested workouts via a coordinating device and ensuring that the user can track their workouts with any number of coordinated devices.

Portions of the system and methods described herein may be implemented using one or more programs or suitable software code, such as the workout application on the coordinating device and the fitness tracking program on the server, both described above, each of which may reside within the memory of the respective computing devices as software or firmware. Such programs and code may be stored in the memory and executed by the processor of the display device or a system server or other computer in communication with the display device. A computer program product implementing an embodiment disclosed herein may therefore comprise one or more computer-readable storage media storing computer instructions translatable by processing circuitry/logic, a CPU, or other data processing device to provide an embodiment of a system or perform an embodiment of a method disclosed herein. Computer instructions may be provided by lines of code in any of various languages as will be recognized by those of ordinary skill in the art.

A "computer-readable medium" may be any type of data storage medium that can store computer instructions and/or data, including, read-only memory (ROM), random access memory (RAM), hard disks (HD), data cartridges, data backup magnetic tapes, floppy diskettes, flash memory, optical data storage, CD-ROMs, or the like. The computer-readable medium can be, by way of example, only but not by limitation, an electronic, magnetic, optical, electromagnetic, infrared, or semiconductor system, apparatus, system, device, or computer memory. The computer-readable medium may include multiple computer-readable media storing computer executable instructions, such as in a distributed system or instructions stored across an array. A "non-transient computer-readable medium" may be any type of data storage medium that can store computer instructions, including, but not limited to the memory devices discussed above.

In the foregoing description, various operations may be described as multiple discrete actions or operations in turn, in a manner that may be helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

The foregoing detailed description of one or more exemplary embodiments of the fitness tracking system with workout coaching has been presented herein by way of example only and not limitation. It will be recognized that there are advantages to certain individual features and functions described herein that may be obtained without incorporating other features and functions described herein. Moreover, it will be recognized that various alternatives, modifications, variations, or improvements of the above-disclosed exemplary embodiments and other features and functions, or alternatives thereof, may be desirably combined into many other different embodiments, systems or applications. Presently unforeseen or unanticipated alternatives, modifications, variations, or improvements therein may be subsequently made by those skilled in the art which are also intended to be encompassed by the appended claims. Therefore, the spirit and scope of any appended claims should not be limited to the description of the exemplary embodiments contained herein.

In another embodiment, a permanent copy of the programming instructions for individual ones of the aforementioned applications may be placed into permanent storage devices (such as e.g., memory) during manufacture thereof, or in the field, through e.g., a distribution medium (not shown), such as a compact disc (CD), or through communication interface (from a distribution server). That is, one or more distribution media having an implementation of the agent program may be employed to distribute the agent and program various computing devices.

It will be appreciated that the various ones of the foregoing aspects of the present disclosure, or any parts or functions thereof, may be implemented using hardware, software, firmware, tangible, and non-transitory computer-readable or computer usable storage media having instructions stored thereon, or a combination thereof, and may be implemented in one or more computer systems.

It will be apparent to those skilled in the art that various modifications and variations can be made in the disclosed embodiments of the disclosed device and associated methods without departing from the spirit or scope of the disclosure. Thus, it is intended that the present disclosure covers the modifications and variations of the embodiments disclosed above provided that the modifications and variations come within the scope of any claims and their equivalents.

What is claimed is:

1. A method for coordinating delivery of suggested workouts to a user, comprising: obtaining a plurality of training plans from a fitness tracking system;
    obtaining user input identifying a selected training plan from the plurality of training plans;
    obtaining one or more suggested workouts corresponding to the selected training plan;
    providing the one or more suggested workouts to a first coordinated personal device of a community of coordinated personal devices;
    obtaining a first workout data record indicating a completion status of a first suggested workout of the one or more suggested workouts, wherein the first workout data record comprises captured workout metrics;
    providing the first workout data record to the fitness tracking system; and
    re-assessing the selected training plan based at least in part on the first workout data record, wherein re-assessing the selected training plan is based on at least one captured workout metric compared to an expected physiological progress, and wherein the expected physiological progress is based on a model of performance progression that is crowdsourced from a community of users.

2. The method of claim 1, further comprising providing a second suggested workout to a second coordinated device of the community of personal devices; and
    receiving a second workout data record.

3. The method of claim 1, further comprising modifying at least one suggested workout associated with the selected training plan.

4. The method of claim 3, wherein the modifying the at least one suggested workout comprises modifying a goal, a date, or a performance metric.

5. The method of claim 1, further comprising matching the first workout data record to the first suggested workout based on a unique workout identifier or a data content.

6. The method of claim 1, wherein providing the one or more suggested workouts to the first coordinated personal device comprises:
    checking an availability of the first coordinated personal device; and
    sending the one or more suggested workouts to the first coordinated personal device when available.

7. A method for suggesting workouts to a user, comprising:
    providing a plurality of training plans to a coordinating device;
    obtaining a user selected training plan;
    providing a plurality of suggested workouts to the coordinating device based on the user selected training plan;
    obtaining a plurality of workout data records from the coordinating device, wherein the plurality of workout data records comprises captured workout metrics;
    each of the plurality of workout data records corresponding to a respective one of the plurality of suggested workouts;
    matching the plurality of workout data records to their corresponding respective one of the plurality of suggested workouts based on an identified similarity; and
    re-assessing the user selected training plan based on the plurality of workout data records, wherein re-assessing the user selected training plan is based on at least one captured workout metric compared to an expected physiological progress, and wherein the expected physiological progress is based on a model of performance progression that is crowdsourced from a community of users.

8. The method of claim 7, wherein the user selected training plan is based on a user workout history.

9. The method of claim 7, wherein the identified similarity comprises: a unique workout identifier, goal, or performance metrics.

10. The method of claim 7, wherein the plurality of workout data records are generated by a community of personal devices in communication with the coordinating device; and
    wherein the method further comprises reconciling data records generated by different devices in the community of personal devices from the plurality of workout data records.

11. The method of claim 10, wherein the reconciling the data records is based on a hierarchical priority of the community of personal devices.

12. The method of claim 7, wherein the identified similarity is based on multi-variate matching logic.

13. The method of claim 7, wherein the plurality of workout data records comprises completion statuses; and
    wherein the re-assessing the user selected training plan is further based on at least one completion status.

14. The method of claim 7 wherein the model of performance progression is based on a group of other users having similar physiological traits to that of the user.

15. A non-transitory computer-readable medium comprising one or more instructions, which when executed by a processor, causes a user apparatus to:
    obtain one or more suggested workouts corresponding to a selected training plan;
    provide the one or more suggested workouts to a first coordinated device of a community of coordinated personal devices;
    receive a first workout data record indicating an intended completion status of a first suggested workout of the one or more suggested workouts, wherein the first workout data record comprises captured workout metrics;

provide the intended completion status to a fitness tracking system; and re-assess the selected training plan based at least in part on the first workout data record, wherein re-assessing the selected training plan is based on at least one captured workout metric compared to an expected physiological progress, and wherein the expected physiological progress is based on a model of performance progression that is crowdsourced from a community of users.

16. The non-transitory computer-readable medium of claim 15, further comprising the one or more instructions, which when executed by the processor, causes the user apparatus to send a notification to a user of the one or more suggested workouts via a user interface.

17. The non-transitory computer-readable medium of claim 16, further comprising the one or more instructions, which when executed by the processor, causes the user apparatus to return a completed workout data record that augments the intended completion status when the first suggested workout was performed differently than suggested.

18. The non-transitory computer-readable medium of claim 17, further comprising the one or more instructions, which when executed by the processor, causes the user apparatus to:

responsive to the user accepting the first suggested workout, capture one or more workout metrics via a sensor.

19. The non-transitory computer-readable medium of claim 15, further comprising the one or more instructions, which when executed by the processor, causes the user apparatus to:

determine an availability of the first coordinated device of the community of personal devices; and push the first suggested workout to the first coordinated device when available.

20. The non-transitory computer-readable medium of claim 15, further comprising the one or more instructions, which when executed by the processor, causes the user apparatus to:

responsive to matching the first workout data record from the first coordinated device with the first suggested workout, return the first workout data record and an identification of a match.

* * * * *